(12) United States Patent
Tsai et al.

(10) Patent No.: US 10,934,355 B2
(45) Date of Patent: Mar. 2, 2021

(54) METHODS AND COMPOSITIONS FOR THE PREVENTION AND TREATMENT OF SURGICAL ADHESIONS

(71) Applicant: The Board of Trustees of the Leland Stanford Junior University, Stanford, CA (US)

(72) Inventors: Jonathan Tsai, Saratoga, CA (US); Nathaniel Fernhoff, Stanford, CA (US); Rahul Sinha, Los Altos, CA (US); Yuval Rinkevich, Munich (DE); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 90 days.

(21) Appl. No.: 16/079,927

(22) PCT Filed: May 1, 2017

(86) PCT No.: PCT/US2017/030454
§ 371 (c)(1),
(2) Date: Aug. 24, 2018

(87) PCT Pub. No.: WO2017/190148
PCT Pub. Date: Nov. 2, 2017

(65) Prior Publication Data
US 2019/0048077 A1    Feb. 14, 2019

Related U.S. Application Data

(60) Provisional application No. 62/329,666, filed on Apr. 29, 2016.

(51) Int. Cl.
| | |
|---|---|
| C07K 16/28 | (2006.01) |
| A61K 38/17 | (2006.01) |
| A61P 41/00 | (2006.01) |
| A61K 39/00 | (2006.01) |
| A61K 45/00 | (2006.01) |
| A61K 38/05 | (2006.01) |
| A61K 38/16 | (2006.01) |
| A61K 31/198 | (2006.01) |
| A61K 31/343 | (2006.01) |
| A61K 31/473 | (2006.01) |
| A61K 31/7004 | (2006.01) |
| A61K 49/00 | (2006.01) |
| C07K 16/30 | (2006.01) |
| A61K 45/06 | (2006.01) |
| A61K 38/00 | (2006.01) |

(52) U.S. Cl.
CPC ........ *C07K 16/2803* (2013.01); *A61K 38/177* (2013.01); *A61K 38/1764* (2013.01); *A61K 39/001168* (2018.08); *A61P 41/00* (2018.01); *A61K 31/198* (2013.01); *A61K 31/343* (2013.01); *A61K 31/473* (2013.01); *A61K 31/7004* (2013.01); *A61K 38/00* (2013.01); *A61K 38/05* (2013.01); *A61K 38/164* (2013.01); *A61K 45/00* (2013.01); *A61K 45/06* (2013.01); *A61K 49/0002* (2013.01); *A61K 2039/505* (2013.01); *A61K 2039/507* (2013.01); *C07K 16/30* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,639,468 A | 6/1997 | Rodgers | |
| 7,592,426 B2 * | 9/2009 | Ebel | C07K 16/30 530/387.3 |
| 8,268,970 B2 * | 9/2012 | Terrett | A61K 47/6857 530/387.1 |
| 8,460,660 B2 * | 6/2013 | Ho | C07K 16/30 424/130.1 |
| 2004/0131600 A1 | 7/2004 | Diamond et al. | |
| 2005/0119216 A1 | 6/2005 | Jackson et al. | |
| 2005/0244415 A1 | 11/2005 | Matozaki et al. | |

(Continued)

FOREIGN PATENT DOCUMENTS

WO    1999/20297    4/1999

OTHER PUBLICATIONS

Tsai et al., Surgical adhesions in mice are derived from mesothelial cells and can be targeted by antibodies against mesothelial markers. Sci. Transl. Med. 10, eaan6735 (2018).*

(Continued)

*Primary Examiner* — Marianne P Allen
(74) *Attorney, Agent, or Firm* — Pamela J. Sherwood; Bozicevic, Field & Francis LLP

(57) ABSTRACT

Aspects of the present disclosure include methods of treating a subject to reduce adhesion formation, the method comprising administering to a subject in need of thereof an agent that that targets adhesion-formation by injured mesothelial cells. The agent can act at a variety of checkpoints in the development of adhesions by injured mesothelial cells, including: targeting the injured mesothelial cells for destruction, recruiting inflammatory macrophages to the site of adhesion, preventing neutrophil recruitment to the site of adhesion, and/or inhibiting the expression or activity of a gene product whose expression is induced in the injured mesothelial cells. Compositions and kits for performing the methods are also provided.

6 Claims, 21 Drawing Sheets

(56) References Cited

U.S. PATENT DOCUMENTS

| | | |
|---|---|---|
| 2011/0044937 A1 | 2/2011 | Bell et al. |
| 2012/0107933 A1 | 5/2012 | Ho et al. |
| 2015/0071905 A1* | 3/2015 | Ring .................. C07K 16/2803 424/94.6 |
| 2015/0250928 A1 | 9/2015 | Obayan |

OTHER PUBLICATIONS

Nair et al. (2013) "Towards Gene Therapy of Postoperative Adhesions: Fiber and Transcriptional Modifications Enhance Adenovirus Targeting towards Human Adhesion Cells", Gynecologic and Obstetric Investigation, pp. 119-124.

Lopes et al. (2008) "Keratinocyte growth factor: a new mesothelial targeted therapy to reduce postoperative pericardial adhesion" European Journal of Cardio-Thoracic, pp. 313-318.

Maciver et al., "Intra-abdominal adhesions: Cellular mechanisms and strategies for prevention", International Journal of Surgery, Sep. 23, 2011, pp. 589-594, vol. 9, Issue 8, Elsevier, New York City, NY.

\* cited by examiner

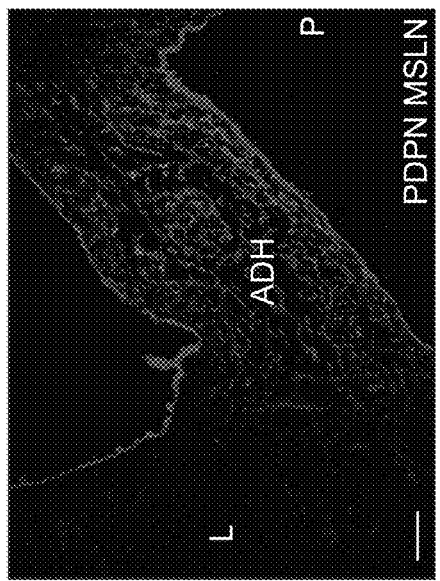
FIG. 1A
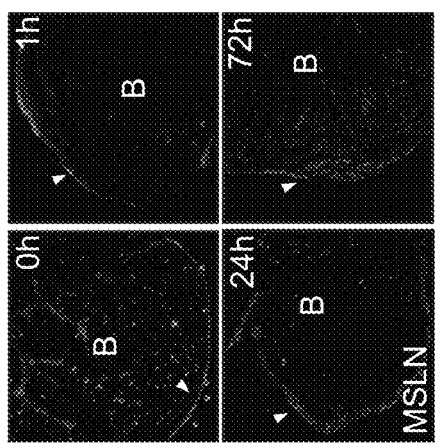
FIG. 1B
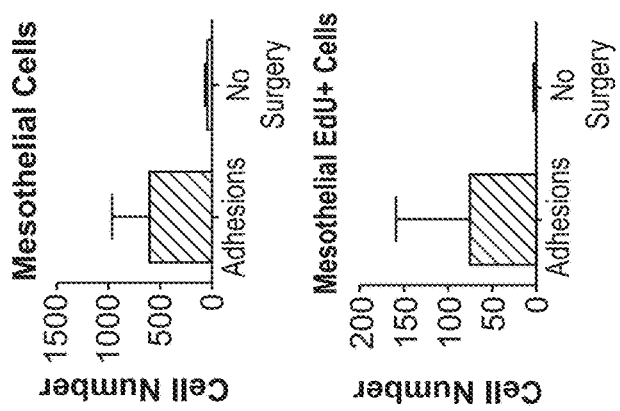
FIG. 1C
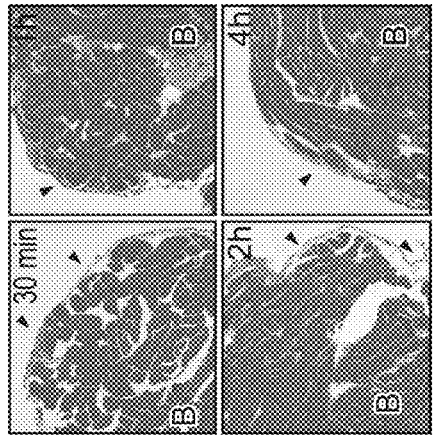
FIG. 1E
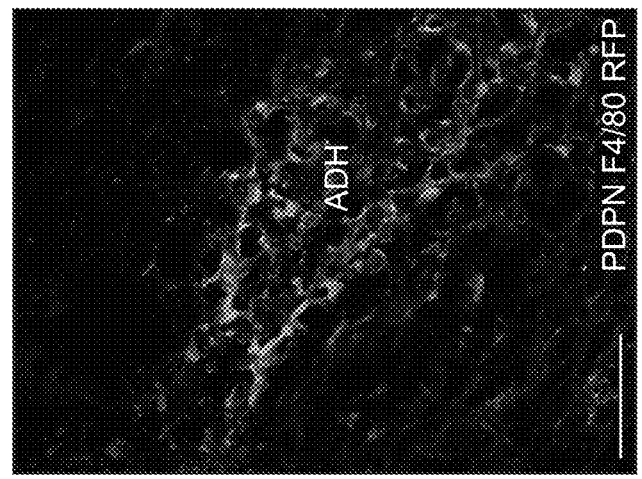
FIG. 1D
FIG. 1F

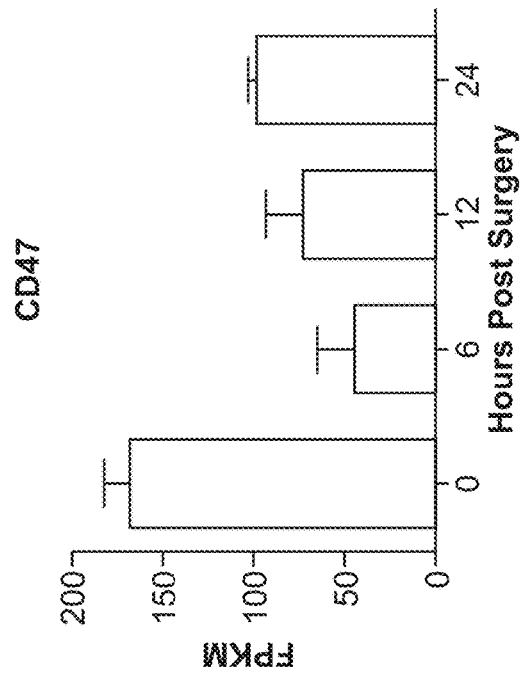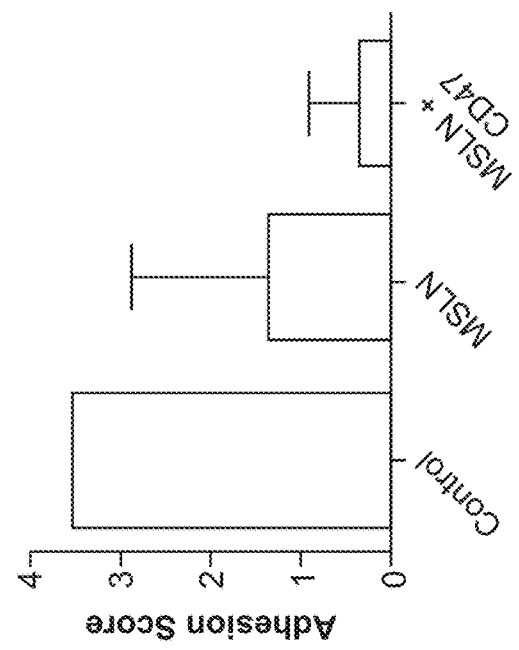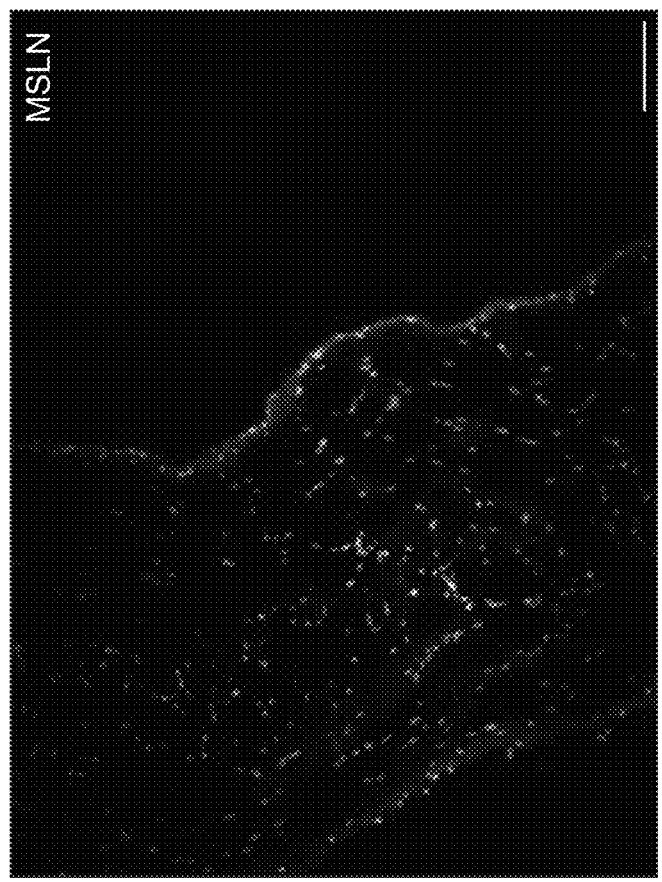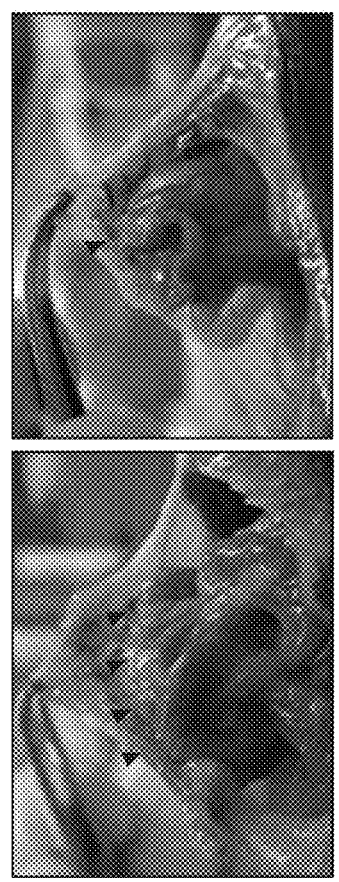
FIG. 4A  FIG. 4B  FIG. 4C  FIG. 4D  FIG. 4E

FIG. 6A                 FIG. 6B

METHODS AND COMPOSITIONS FOR THE PREVENTION AND TREATMENT OF SURGICAL ADHESIONS

CROSS REFERENCE

This application is a 371 application and claims the benefit of PCT Application No. PCT/US2017/030454, filed May 1, 2017, which claims benefit of U.S. Provisional Patent Application No. 62/329,666, filed Apr. 29, 2016, which applications are incorporated herein by reference in their entirety.

FEDERALLY SPONSORED RESEARCH AND DEVELOPMENT

This invention was made with Government support under contracts GM007365 and DK108561 awarded by the National Institutes of Health. The Government has certain rights in the invention.

BACKGROUND OF THE INVENTION

Adhesions are fibrous tissues that develop as the result of trauma to the peritoneum, either due to physical trauma (often due to surgery), or major inflammatory insults (peritonitis, infection, etc). Although many adhesions are asymptomatic, their primary sequelae include bowel obstruction, female infertility (when occurring on or near the uterus), chronic pain, and poor quality of life. The National Institutes of Health estimate that over 93% of patients having undergone abdominal surgery progress to adhesion formation. Current estimates suggest that up to 20% of patients following abdominal surgery are readmitted to hospitals due to post-operative adhesion formation and project the healthcare cost to be well over $1 billion in the United States alone, rivaling that of many cancers. Still, no definitive strategies exist to prevent adhesion formation, underscoring the notion that adhesions present a significant healthcare burden and treatment and prevention should be an ongoing medical priority.

Extensive studies on the pathogenesis of adhesion formation focused on inflammatory infiltration and a balance between fibrin deposition and fibrinolysis. Currently it is believed that damage to the peritoneal surface initiates a complex cascade that recruits inflammatory cells through a panel of cytokine signals. Meticulous studies have been done to map the kinetics of the cellular infiltrate: polymorphonuclear leukocytes (PMNs) are present early on (within 6 hours) of injury, followed by macrophage entry (persisting over 72 hours) and later stage recruitment of T and B-cells. The roles of each of these cell types in adhesion formation have been explored, and most studies agree that the pro-inflammatory profiles of PMNs, macrophages, and CD4+ T-cells serve to exacerbate the severity of the adhesions.

More work has been done on the contribution of the coagulation cascade as a key driver of the adhesion process. The coagulation cascade is activated concurrently with immune cell infiltration. Thrombin converts fibrinogen to fibrin, which form deposits on the surface of organs shortly after mesothelial injury and organize into fibrin lattices for wound healing or adhesion development.

The current state of knowledge stipulates that peritoneal or organ injury sufficient to produce adhesions requires the removal of the surface mesothelium (diZerega & Campeau; Richardson, 1911; Schade & Williamson, 1968; A. Suzuki, 2015) exposing their underlying basement membranes which leads to fibrin attachments between two denuded surfaces and is followed by accumulations of fibroblasts, from an unknown origin. Since these observations have been largely dependent on classic snap-shot histological examinations, and because of the difficulties in identifying cell type, the source of new invading fibroblast cells, has been a matter of debate. Among the possible sources are metaplasia of myofibroblasts within the connective tissue beneath the surfaces, the expansions of mesenchymal stem cells (MSCs), the invasion of undifferentiated primitive MSCs, or to the deposition of extracellular matrix by subperitoneal fibroblasts leading to formation of adhesions (Cheong et al.; Ellis, Harrison, & Hugh, 1965; Hellebrekers & Kooistra, 2011; Lucas, Warejcka, Young, & Lee, 1996; Raftery, 1973).

Following the above paradigms, investigators have transplanted the mentioned fibroblast cell types into the abdominal cavities of rodent models at different times after surgery and consequently showing increased formation of postoperative adhesions, and claiming to support the notion that adhesions arise from these cell types (Lucas et al., 1996). Others have indicated that the epithelial characteristics of the surface mesothelium, including its frictionless interface, point to a protective role against adhesion formation, and have even proposed the use of mesothelium cell sheets as a clinical approach for preventing postoperative adhesions (Inagaki, Inagaki, Kokudo, & Miyajima, 2015).

In the absence of a cell-of-origin that can be used to study fibrotic disease initiation and progression (Rinkevich et al., 2012, 2015), not much is known about the early molecular and cellular events leading up to abdominal adhesions, and therefore no robust preventative or postsurgical treatments have been developed. Hence, current clinical treatments use physical barriers to prevent contact between adjacent organs as a preventative treatment ((Liu, Li, Shu, Gray, & Prestwich, 2005), or adhesion lysis that requires a physician to surgically separate the adhered organs, a tactic hampered by a high rate of adhesion reformation (Ray, 1998).

The mesothelium is the outer epithelial monolayer that lines all serous cavities (the pleural, pericardial and peritoneal cavities) of the mammalian body and the outer surfaces of various internal organs. Although the primary architecture of the mesothelium is that of a squamous epithelium, the tissue also expresses cytological and biochemical features that are characteristic of a fibroblast cell type (Michailova & Usunoff, 2006) rendering the mesothelium with remarkable cellular plasticity (Rinkevich et al., 2012). For example, it has been suggested that the mesothelial cells respond to cytokines and other signals and can take on a myofibroblastic phenotype, secreting cytokines and extracellular matrix proteins, which exacerbates the adhesion process. Recent lineage tracing studies further demonstrate the plasticity of surface mesothelium to generate fibroblast and smooth muscle cell types for the internal organs and their vasculature.

While a number of different reports have suggested that ischemia, physical trauma, hemorrhage, temperature, chemical damage, and tissue desiccation are initiating factors in adhesion formation, the underlying molecular and genetic mechanisms that regulate adhesion pathogenesis have not been defined. The present disclosure provides insights into the molecular and genetic mechanisms of adhesion formation and thereby provides, inter alia, therapeutic treatments based on these findings.

SUMMARY OF THE INVENTION

The present disclosure demonstrates that the surface mesothelium represents the tissue-of-origin for adhesion formation, identifying adhesions as a gross pathologic manifestation of mesothelium cells themselves. It also provides the molecular chain of events leading normal mesothelium towards an adhesion program and demonstrates that functional disruption of these pathways curtail adhesion formation in vivo. These results provide a new pathomechanistic understanding of adhesion formation and establish novel therapeutic tactics/avenues that treat and/or prevent adhesion pathogenesis.

In certain embodiments, the present disclosure provides methods of treating a subject to reduce adhesion formation, the method comprising administering to a subject in need of thereof an agent that that targets adhesion-formation by injured mesothelial cells. In certain embodiments, the agent targets the injured mesothelial cells for destruction. In certain embodiments, the agent recruits inflammatory macrophages to the site of adhesion. In certain embodiments, the agent prevents neutrophil recruitment to the site of adhesion. In certain embodiments, the agent inhibits the expression or activity of a gene product whose expression is induced in the injured mesothelial cells. Non limiting examples of agents include: an anti-mesothelin antibody or mesothelin binding fragment thereof; an anti-CD47 antibody, a signal regulatory protein alpha (SIRPα) polypeptide, or a CD47 binding fragment of either; monocyte chemoattractant protein-1 (MCP-1) or an inflammatory macrophage recruiting portion thereof; an anti-Gr-1 antibody or Gr-1 binding fragment thereof or other marker involved in depletion of granulocytes; thioglycolate; PLGA; mannose or mannose conjugated to a binding moiety specific for injured mesothelium including UPKB1-binding moiety or MSLN binding moiety; and any combination thereof. Included are peptide, peptoid, RNA, DNA, PNA, or other engineered molecule selected for binding for injured mesothelium, e.g. for UPKB1, MSLN, etc.

Applicants have identified biological markers that are expressed selectively on injured mesothelium at the time of adhesion formation, which marker include without limitation MSLN, UPK1B, etc. The markers provide targets for removal or destruction of injured mesothelial cells, for example by apoptosis, phagocytosis, necrosis, etc. In some embodiments a specific binding moiety, e.g. an antibody or fragment thereof, is administered to an individual to remove injured mesothelial cells, e.g. to prevent adhesion formation, to reduce ongoing adhesion formation, or to reduce existing adhesions. The markers are useful biomarkers for the presence of injured mesothelial cells, e.g. by PET, MRI, etc. In some embodiments an antibody or other specific binding moiety that binds to an injured mesothelial cell marker, including without limitation MSLN or UPK1B, is labeled with a detectable marker. The marker may include, for example, moieties useful in PET or MRI imaging. The lebeled antibody or other specific binding moiety is contacted with the patient, for example by iv or other delivery system, and the presence of the labeled moiety used to image the cells involved in adhesion formation.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1F: The surface mesothelium proliferates in response to adhesion induction. FIG. 1A Haematoxylin and eosin (H&E) stains of ischemic buttons (B) after 30 minutes, 1 hour, 2 hours and 4 hours following placement and abrasion show the continued immediate presence of the peritoneal mesothelium (arrow). FIG. 1B Immunofluorescence staining for mesothelin (MSLN) of ischemic buttons 1 hour, 24 hours, 72 hours, and immediately after placement and abrasion confirm and show prolonged presence of the mesothelium, and potential thickening from a single cell layer after 24 and 72 hours. FIG. 1C Immunofluorescence staining for MSLN and podoplanin (PDPN), mesothelial specific markers, 7 days after adhesion induction show a fully formed string adhesion between the liver (L) and peritoneum (P). FIG. 1D Immunofluorescence staining for PDPN and F4/80 of adhesions from wild type and RFP$^+$ parabionts. FIG. 1E Numbers of mesothelial cells (MSLN+) (top) and double positive EdU+MSLN+ mesothelial cells (bottom) were counted per high powered field (0.75 mm×1 mm) (n=20) in normal peritoneal tissue versus adhesed peritoneal tissue. Significantly more mesothelial and double positive cells were observed in the adhesion sites versus normal peritoneal tissue. FIG. 1F Immunofluorescence staining for MSLN and EdU of normal peritoneum (P) (top) and adhesions (ADH) between the peritoneum and large intestine (I).

FIG. 2A Surface mesothelium was isolated from ischemic buttons and purified by a PDPN$^+$LYVE1$^-$CD31$^-$CD45$^-$ surface phenotype. FIG. 2B-2C Heatmap of RNA sequencing of purified surface mesothelium immediately after and 6 hours, 12 hours, and 24 hours after button placement clustered by gene expression. Representative genes are shown above clusters. FIG. 2D-2E Log fold changes in transcript levels were calculated for each 6, 12, and 24 hours post adhesion induction surgery in comparison to the control and plotted against all genes found in the genome. FIG. 2F Heatmap of genesets upregulated or downregulated in activated surface mesothelium 6, 12, and 24 hours post adhesion induction. FIG. 2G Expression levels (FPKM) of target genes categorized by embryonic mesothelium, fibroblast, or adhesion molecules over a 24 hour time course from RNA sequencing. FIG. 2H Validation of target genes via immunofluorescence stains of adhesed tissue 7 days post induction. All scale bars are 100 μm.

FIG. 3A An adhesion score of 0 shows no visible adhesion to the ischemic button (B). Little proliferation is visible on H&E and hoechst stain and the button stains positive for MSLN and fibronectin. FIG. 3B An adhesion score of 1 is a slight string adhesion to the ischemic button with fibrous, nucleated tissue on H&E and hoechst stain. The string adhesion stains positive for MSLN and fibronectin. FIG. 3C Adhesions with scores of 2 show direct attachment of one area of an organ to the ischemic button with identifiable delineation of the ischemic button on H&E and hoescht staining and stain positive for MSLN, fibronectin, and F4/80. FIG. 3D Adhesion scores of 3 show direct attachment of two non-continuous areas of one organ or two areas of two organs to the ischemic button with two identifiable areas on H&E and hoescht stain and stain positive for MSLN, fibronectin, F4/80, pan collagen, and CD31. FIG. 3E Adhesion scores of 4 show direct attachment of three or more non-continuous areas to the ischemic button. Organ specific mesothelium is often hard to identify on H&E and hoescht stains, and adhesion areas stain for MSLN, fibronectin, F4/80, pan collagen, CD31. FIG. 3F Adhesion scores of 5 show complete compacted abdomens with attachments between the peritoneum and organs as well as systemic attachments between organs on H&E and hoescht stains. All scale bars are 100 um.

FIG. 4A-4F: Anti-mesothelin antibodies resolve adhesions. FIG. 4A Immunofluorescence stains show anti-MSLN antibodies injected intraperitoneally bind to the injured mesothelial surface immediately after adhesion induction in vivo. FIG. 4B CD47 is expressed 6, 12, and 24 hours following adhesion induction, as well as in normal states. FIG. 4C Adhesions are present two weeks after induction and treatment using vehicle controls. FIG. 4D Treatment with anti-MSLN antibodies alone show significant decreases in adhesions. FIG. 4E Anti-CD47 treatment with anti-MSLN antibodies improves clearance of adhesions. FIG. 4F Immunofluorescent stains of collagen, fibronectin, CD31, F4/80, and MSLN reveal removal of MSLN+ cells.

FIG. 5A In vitro mesothelial macrophage co-cultures in normal oxygen conditions stained for PDPN or HIF1A. FIG. 5B In vitro mesothelial macrophage co-cultures in hypoxia (5% O2 incubator) stained for PDPN or HIF1A. Scale bars are 250 um. FIG. 5C Immunofluorescence stains show adhesions are HIF1A+ 7 days after induction. FIG. 5D Immunofluorescence stains show adhesions are HIF1A– 7 days after induction and treatment with small molecular inhibitors. All scale bars are 100 um. FIG. 5E Treatment with Hif1α small molecule inhibitors echinomycin and PX12 show significant decreases in adhesion formation by downregulating Hif1α. FIG. 5F Expression levels from RNA sequencing of selected target genes during a 24 hour time course following adhesion induction and after echinomycin treatment. Heatmap of RNA sequencing of purified surface mesothelium immediately after and 6 hours, 12 hours, 24 hours and with echinomycin treatment after button placement clustered by gene expression.

FIG. 6A-6C: Human peritoneal adhesions share similar expression of target genes. FIG. 6A H&E stains of human adhesion tissue. FIG. 6B Trichrome stains of human adhesion tissue. FIG. 6C Immunofluorescence and in situ hybridization stains of human adhesion tissue. Scale bars are all 100 um unless otherwise noted.

FIG. 9A RNA sequencing results from injured mesothelial cells over a 24 hour time course shows differential expression of multiple genesets and processes, including inflammatory chemokines and cytokines. FIG. 9B Fluorescence microscopy of an adhesion induced in parabiosis experiments between a mouse constitutively expressing the red fluorescent protein mCherry ("TM7") and a wild type (non-colored mouse). F4/80 is shown in green. FIG. 9C Fluorescence microscopy of an adhesion induced in constitutive cyan fluorescent protein (CFP) mice ("Host") receiving bone marrow transplants from constitutive mCherry mice (TM7 "Donor"). F4/80 is shown in green. FIG. 9D Adhesion score of mice pre-treated with thioglycollate and catalase (24 hours prior to adhesion induction) as well as treatment with MCP-1, anti-GR-1 antibody, or both, for three days following adhesion induction surgery.

DEFINITIONS

Figure 2A:
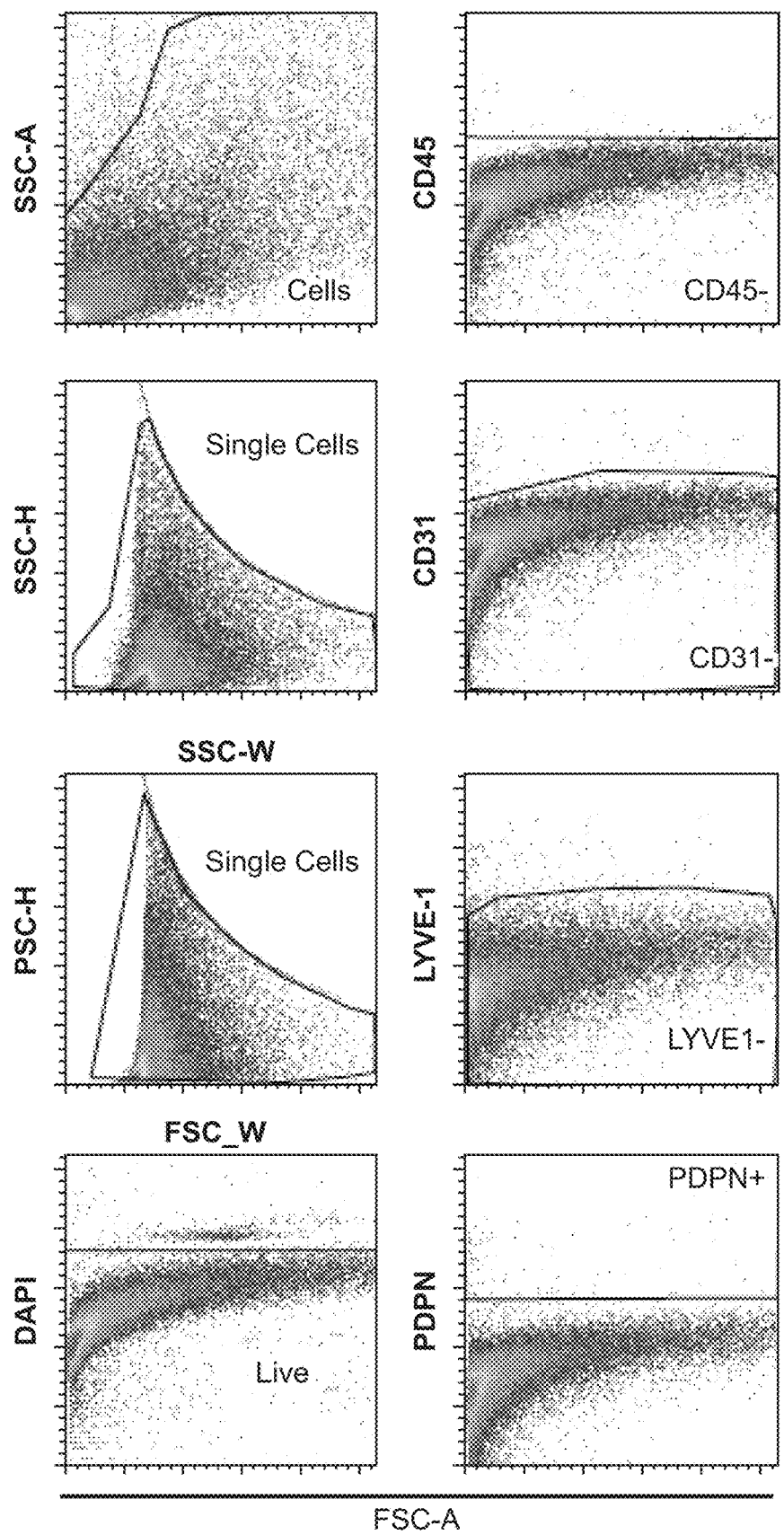
FIG. 2A-2H.

In the description that follows, a number of terms conventionally used in the field of cell culture are utilized. In order to provide a clear and consistent understanding of the specification and claims, and the scope to be given to such terms, the following definitions are provided.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

The term "therapeutic agent" as used herein includes one or more "therapeutic agents" or "drugs." The terms "therapeutic agents" or "drugs" can be used interchangeably herein and include pharmaceutically active compounds. Examples include, without limitation: antibiotics, small molecules, proteins or polypeptides, polynucleotides, nucleic acids, oligonucleotides, ribozymes, anti-sense oligonucleotides, gene/vector systems, antisense nucleic acid (RNA or DNA), virus vectors or vectors derived from viral sources, antibodies, receptor antagonists, transcriptional repressors, etc. Polynucleotides can code for therapeutic proteins or polypeptides.

"Polynucleotide" or "oligonucleotide" is used interchangeably and each means a linear polymer of nucleotide monomers, e.g., deoxyribonucleotides and/or ribonucleotides.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. An amino acid analog refers to a compound that has the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies or monoclonal antibodies. In certain aspects, monoclonal antibodies may be preferable because they may be reproduced by cell culture or recombinantly, and can be modified to reduce their antigenicity. The production of polyclonal and monoclonal antibodies is well known in the art.

In addition to entire immunoglobulins (or their recombinant counterparts), immunoglobulin fragments comprising the epitope binding site (e.g., Fab', F(ab')2, or other fragments) are useful as antibody moieties in the present invention and are sometimes referred to as "binding fragments" or "epitope binding fragmnets" of an antibody. Such antibody fragments may be generated from whole immunoglobulins by ricin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Antibodies include free antibodies and antigen binding fragments derived therefrom, and conjugates, e.g. pegylated antibodies, drug, radioisotope, or toxin conjugates, and the like. Monoclonal antibodies directed against a specific epitope, or combination of epitopes, will allow for the targeting and/or depletion of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like.

Humanized versions of such antibodies are also within the scope of this invention. Humanized antibodies are especially useful for in vivo applications in humans due to their low antigenicity.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having or at risk of having an adhesion. Subjects may be human, but also include other mammals, particularly those mammals useful as laboratory models for human disease, e.g. mouse, rat, etc.

As used herein, the terms "treatment," "treating," and the like, refer to administering an agent, or carrying out a procedure, for the purposes of obtaining an effect in a subject (e.g., a patient). The effect may be prophylactic in terms of completely or partially preventing an undesirable condition, disease or symptom thereof and/or may be therapeutic in terms of effecting a partial or complete remedy, remission, or cure for an undesirable condition, disease and/or symptoms of the disease. Treating thus encompasses the dinistration of an agent before an undesirable condition, disease or symptom thereof occurs, during the development of an undesirable condition, disease or symptom thereof, and/or after an undesirable condition, disease or symptom thereof has occurred. Treating may refer to any indicia of success in the treatment or amelioration or prevention of an undesirable condition or disease, including any objective or subjective parameter such as abatement; remission; diminishing of symptoms or making the undesirable condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present disclosure to prevent or delay, to alleviate, or to arrest or inhibit development of the symptoms or undesirable condition. The term "therapeutic effect" refers to the reduction, elimination, or prevention of the undesirable condition, disease, or symptoms or side effects of thereof.

"In combination with", "combination therapy" and "combination products" refer, in certain embodiments, to the concurrent administration to a patient of a first therapeutic and a second therapeutic. When administered in combination, each component can be administered at the same time or sequentially in any order at different points in time. Thus, each component can be administered separately but sufficiently closely in time so as to provide the desired therapeutic effect.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject, is sufficient to effect treatment of an undesirable condition, symptom, or disease of the subject. The effective dose is sufficient to reduce adhesions by at least about 10%, at least about 20%, at least about 30%, at least about 40%, at least about 50%, at least about 60%, at least about 70%, at least about 80%, at least about 90%, or more. The dose of a therapeutic antibody, for example, may be from about 1 mg/kg body weight to about 100 mg/kg body weight, and may be administered immediately following surgery or other event expected to result in adhesion formation; or for reducing existing adhesions. Dosing may be repeated daily, every 2 days, every 3 days, semi-weekly, weekly, etc.

DETAILED DESCRIPTION OF THE EMBODIMENTS

As summarized above, the present disclosure provides methods for treating surgical adhesions in a subject, which includes, e.g., preventing adhesion formation, halting or reducing the formation of adhesions, and/or reversing or eliminating established adhesions in a subject. Composition and kits are also provided for performing such methods.

Before aspects of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The present disclosure relates to methods for treating a subject to reduce adhesion formation, e.g., surgical adhesions, and includes administering to a subject an agent that that targets adhesion-formation by injured mesothelial cells. Compositions and kits configured to perform such treatment methods are also provided. The disclosure is based, at least in part, on our identification of the surface mesothelium as a primary cell type responsible for initiating and contributing towards adhesions (see Examples below). We demonstrate that adhesion formation can be treated in subjects by targeting one or more of multiple different checkpoints in the adhesion formation process by injured mesothelial cells.

In certain embodiments, the agent targets the injured mesothelial cells for destruction. For example, the agent may bind to a gene product whose expression is induced in the injured mesothelial cells, thereby differentiating it from un-injured mesothelial cells and allowing it to be eliminated. In some of these embodiments, the agent is specific for (e.g., specifically binds to) a target protein that is expressed in injured mesothelial cells but not in un-injured mesothelial cells. In certain embodiments, the gene product is mesothelin (MSLN) or uroplakin 1B (UPK1B), both of which are discussed in further detail below.

As described in the Examples section, the use of agents that target MSLN can increase clearance of post-operative adhesions. In addition, MSLN is a desirable target as it is an embryonic mesothelial gene and is not widely expressed in adult stages, with the notable exclusion of adhesions (as described herein) and tumors.

In certain embodiments, the agent is a polypeptide that specifically binds to MSLN. For example, the polypeptide can be an anti-MSLN antibody or MSLN binding fragment thereof.

The agent can be administered alone or in combination with other agents, e.g., immunomodulatory agents. As such, in certain embodiments, the methods further include administering anti-MSLN antibodies alone or in conjunction with other immune modulators, e.g., agents that induce cell removal. In certain of these embodiments, the second agent inhibits the activity of CD47 in the injured mesothelial cells, e.g., a polypeptide that binds to CD47 and disrupts the binding of CD47 with SIRPα, at a dose that achieves a depletion of injured mesothelial cells. In certain embodiments, the polypeptide is selected from the group consisting of: an anti-CD47 antibody, a signal regulatory protein alpha (SIRPα) polypeptide, a CD47 binding fragment of either, and any combination thereof. See, e.g., U.S. Pat. No. 8,758, 750 entitled "Synergistic anti-CD47 therapy for hematologic cancers"; U.S. Pat. Nos. 8,562,997; 9,623,079; U.S. Patent Application Publication no. US 2015/0071905 entitled "High Affinity Sirp-Alpha Reagents", all of which are hereby incorporated by reference herein in their entirety.

The Examples provided herein demonstrate that the use of polypeptide (e.g., antibody) agents specific for induced gene products in injured mesothelial cells results in the reduction of adhesions in a clinical setting through the elimination of the injured mesothelial cells. Specifically, targeting the cell-surface receptor MSLN with an anti-MSLN antibody shows substantial reduction in adhesion grades in animal models after induction and have demonstrated feasibility due to animals manifesting little or no side effects. The efficacy of treatment is further increased by the use of immune adjuvants, including without limitation anti-CD47.

In certain embodiments, the agent recruits inflammatory macrophages (through recruitment of circulating monocytes) to the site of adhesion. This recruitment results in the reduction of adhesion formation in a clinical setting.

As described in the Examples section, the use of and inflammatory macrophage/monocyte recruiting agents are effective in treating post-operative adhesions in a subject (e.g., preventing or removing). For example, administration of MCP-1 (e.g., intraperitoneally) showed substantial reduction in adhesion grades in animal models after induction. Such administration was demonstrated to be feasible due to animals manifesting little or no side effects.

In addition to MCP-1, agents that induce a sterile inflammation in a subject find use in treating adhesion formation. Examples of such agents include thioglycollate and poly(lactic-co-glycolic acid) PLGA.

Therefore, the recruitment of inflammatory macrophages can be achieved with any convenient agent or agents, including but not limited to: monocyte chemoattractant protein-1 (MCP-1) or an inflammatory macrophage recruiting portion thereof, thioglycolate, PLGA, or any combination thereof.

In certain embodiments, the agent prevents neutrophil recruitment. As described in the Examples section, elimination/reduction of circulating neutrophils or prevention of their migration to potential adhesion sites results in the reduction of adhesion formation in a clinical setting. Thus, any agent that eliminates/reduces circulating neutrophils and/or prevents their migration to potential adhesion sites can be administered to a subject to treat adhesions.

For example, the agent can be a polypeptide that binds to a granulocyte marker selected from Gr-1, CD66b, CD177, CXCR1, VAP1, CXCR2, and CD10, which are expressed on neutrophils and other inflammatory granulocytes, and leads to their elimination/reduction or inhibits their migration to potential adhesion sites. In certain embodiments, the agent is a polypeptide, e.g an antibody or binding fragment thereof.

It is noted that one or more agents that promote inflammatory macrophage recruitment and one or more agents that eliminate/reduce or inhibit neutrophil migration can be combined. For example, anti-MSLN antibody and anti-granulocyte antibody can be administered to a subject to treat adhesions.

In certain embodiments, the agent inhibits the expression or activity of a gene product whose expression is induced in the injured mesothelial cells, e.g. MSLN, UPK1B, etc.

As described in the Examples section, the expression of a number of genes is induced in injured mesothelial cells that can be exploited to treat adhesions in a subject. A number of different agents can be used, each of which may target different induced genes and/or the cellular pathways or cellular activities they regulate. The agent can inhibit gene expression, e.g., an inhibitory RNA agent, e.g., RNAi, shRNA, anti-sense RNA, and the like. The agent can inhibit the activity of the gene product, e.g., preventing its interaction with a receptor/ligand or a signaling molecule in a signal transduction pathway in which the gene product plays a role. No limitation in this regard is intended.

For example, the gene for hypoxia-inducible factor 1-alpha (HIF-1α) is induced upon mesothelial cell injury. Administering an agent that inhibits the expression and/or the activity of HIF-1α to a subject can treat (e.g., prevent, eliminate or reduce) adhesions in the subject. Any agent that inhibits HIF-1α expression or activity can be used, including but not limited to: echinomycin, PX12, FM19G11, cryptotanshinone, chetomin, Bortezumib, acriflavin, methyl 3-[[2-[4-(2-adamantyl) phenoxy] acetyl] amino]-4-hydroxybenzoate, dimethyloxaloylglycine (DMOG), chemotin, YC-1, chrysin, dimethyl-bisphenol A, CL67, and combinations thereof.

For example, as shown herein, echinomycin significantly reduces the formation of adhesions in a mouse model by inhibiting mesothelial cell proliferation, activation, and cell-cell contact. Additional agents that interfere with HIF-1α activity also reduce adhesion formation in these models, including PX12, FM19G11, and cryptotanshinone.

As another example, the gene for uroplakin 1B (UPK1B) is induced upon mesothelial cell injury. Administering an agent that inhibits the expression and/or the activity of UPK1B to a subject can treat (e.g., prevent, eliminate or reduce) adhesions in the subject. Any agent that inhibits UPK1B expression or activity can be used. In addition, agents that target UPK1B expressing cells for destruction or removal. In certain embodiments, the agent is a polypeptide that specifically binds to UPK1B. For example, the polypeptide can be an anti-UPK1B antibody or UPK1B binding fragment thereof. The agent can be administered alone or in combination with other agents, e.g., immunomodulatory agents. As such, in certain embodiments, the methods further include administering anti-UPK1B antibodies alone or in conjunction with other immune modulators, e.g., agents that induce cell removal. In certain of these embodiments, the second agent inhibits the activity of CD47 in the injured mesothelial cells, e.g., a polypeptide that binds to CD47 (as described above). UPK1B is a desirable target as it is an embryonic mesothelial gene and is not widely expressed in the adult except in adhesions (injured mesothelium) and the bladder epithelium.

Mannose is a simple monosaccharide that competitively binds UPK1 B and prevents its interaction with cognate receptor/ligand(s). As shown in the Examples herein, mannose competitively binds to UKP1B and leads to substantial reduction in adhesion scores in animal models after induction. Thus, in certain embodiments, the agent administered to the subject to treat adhesions competitively binds to UPKB1. These agents include, e.g., mannose, a UPKB1-binding derivative thereof (e.g., protein conjugates, dimers, trimers, dendrimers, etc), and/or analogs as well as other agents that competitively bind UPKB1, e.g., soluble polypeptides that bind to UPKB1, e.g., derivded from natural receptor/ligand domains to which UPKB1 binds.

As another example, the expression of a number of neutrophil recruiting gene products are induced in injured mesothelial cells, including CXC chemokines. For example, the CXCL1 and CXCL2 genes are induced in mesothelial cells upon injury. As noted above, the recruitment of neutrophils leads to enhanced adhesion formation, and as such preventing the expression and/or activity of neutrophil recruiting gene products will reduce adhesion formation in a subject. Therefore, in certain embodiments, an agent that inhibits the expression and/or activity of a neutrophil recruiting gene product can be administered to a subject to treat adhesions. In certain embodiments, the gene product is a CXC chemokine, e.g., CXCL1, CXCL2, or combinations thereof. The agent can be an antibody or binding fragment thereof that binds to and inactivates the CXC chemokine or an agent that block expression of the CXC chemokine (e.g., and inhibitory RNA moiety, e.g., siRNA, shRNA, etc.).

The adhesion treatment methods provide herein can be used to treat a subject for any of a variety of conditions that can promote adhesion formation, e.g., post-operative/surgical lesions (e.g., open or laparoscopic surgeries) and/or for treatment after inflammatory insults. The agents can be administered for adhesion prophylaxis, e.g., prior to the formation of an adhesion, or after adhesions have been formed or initiated. Thus, in certain embodiments, the adhesion is an abdominal adhesion, e.g., an abdominal surgical adhesion. The agent can be administered prior to, during, or after the surgical procedure.

According to the present disclosure, adhesion treatments agents as described herein can be provided in pharmaceutical compositions suitable for therapeutic use, e.g. for human treatment. In some embodiments, pharmaceutical compositions of the present disclosure include one or more therapeutic entities of the present disclosure or pharmaceutically acceptable salts, esters or solvates thereof. In some other embodiments, pharmaceutical compositions of the present disclosure include one or more therapeutic entities of the present disclosure in combination with another therapeutic agent, e.g., an anti-inflammatory agent or additional agent for treating an adhesion.

Therapeutic entities of the present disclosure are often administered as pharmaceutical compositions comprising an active therapeutic agent and other pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present disclosure can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

As noted above, methods are provided for treating adhesions in a subject by administering an agent that that targets adhesion-formation by injured mesothelial cells. Such methods include administering to a subject in need of treatment a therapeutically effective amount or an effective dose of one or more agents as detailed herein.

Effective doses of the therapeutic entity of the present disclosure, e.g. for the treatment of adhesions, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present disclosure can be administered on multiple occasions. Intervals between single dosages can be weekly, monthly or yearly. Intervals can also be irregular as indicated by measuring blood levels of the therapeutic entity in the patient. Alternatively, therapeutic entities of the present disclosure can be administered as a sustained release formulation, in which case less frequent administration is required. Dosage and frequency vary depending on the half-life of the polypeptide in the patient.

Compositions for the treatment of adhesions can be administered by parenteral, topical, intravenous, intratumoral, oral, subcutaneous, intraarterial, intracranial, intraperitoneal, intranasal or intramuscular means. A typical route of administration is intravenous or intraperitoneal, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of adhesion treatment agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. It is noted that a number of the adhesion treatment agents disclosed herein are approved for use in humans.

Also within the scope of the disclosure are articles of manufacture (e.g., systems or kits) that contain an adhesion treatment agent or formulations thereof and instructions for use. The kit can further contain a least one additional reagent. Kits typically include a label indicating the intended use of the contents of the kit. The term label includes any writing, or recorded material supplied on or with the kit, or which otherwise accompanies the kit.

As such, aspects of the disclosure include a kit that contain: (a) a pharmaceutical composition having (i) an agent that that targets adhesion-formation by injured mesothelial cells in an amount effective to reduce adhesions (as described herein), and (ii) a pharmaceutically acceptable carrier, and (b) instructions for administering the pharmaceutical composition to a subject who has had or will have surgery. In some embodiments, the the agent is selected from the group consisting of: an anti-MSLN antibody or MSLN binding fragment thereof; an anti-UPKB1 antibody or UPKB1 binding fragment thereof; an anti-CD47 antibody, a SIRPα polypeptide, or a CD47 binding fragment of either; MCP-1 or an inflammatory macrophage recruiting portion thereof; an anti-Gr-1 antibody or Gr-1 binding fragment thereof; thioglycolate; PLGA; mannose or a UPKB1-binding derivative thereof; and any combination thereof.

Also provided are methods of making articles of manufacture (e.g., systems or kits) as described above, e.g., a kit, and that includes combining (a) a pharmaceutical composition having (i) an agent that that targets adhesion-formation by injured mesothelial cells in an amount effective to reduce adhesions (as described herein), and (ii) a pharmaceutically acceptable carrier, and (b) instructions for administering the pharmaceutical composition to a subject who has had or will have surgery. In some embodiments, the the agent is selected from the group consisting of: an anti-MSLN antibody or MSLN binding fragment thereof; an anti-CD47 antibody, a SIRPα polypeptide, or a CD47 binding fragment of either; MCP-1 or an inflammatory macrophage recruiting portion thereof; an anti-Gr-1 antibody or Gr-1 binding fragment thereof; thioglycolate; PLGA; mannose or a UPKB1-binding derivative thereof; and any combination thereof.

The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Peritoneal adhesions are fibrous tissues that tether organs to one another or to the peritoneal wall and are a significant cause of post-surgical and infectious morbidity. Extensive studies have been done and suggest that hematopoietic cells, cytokines, and fibrin deposition play a major role in promoting adhesion formation. However, the molecular pathogenesis initially promoting adhesion formation has not been well characterized.

Here we identify the surface mesothelium as a primary cell type responsible for initiating and contributing towards adhesions. Time courses of mesothelial specific stains and proliferation markers demonstrate that adhesions are formed from mesothelial cell expansion. Isolation and RNA sequencing of activated mesothelial cells in a brief time course immediately following adhesion induction suggest a specific surface marker phenotype of an adhesion, and candidate regulators of adhesion formation. Mesothelin (MSLN) and uroplakin1B (UPK1B) were identified as unique surface receptors on injured mesothelium. Hypoxia inducible factor 1α (HIF1α) was identified as an early regulator, and functional inhibition showed significant diminishing of adhesion formation, suggesting new therapeutic agents to prevent post-operative adhesions. Further RNA sequencing analysis of HIF1α deficient mesothelial cells following adhesion induction demonstrated that targets, such as Wilms Tumor 1 (WT1) and UPK1B are downstream to and controlled by HIF1α and play a role in the adhesion process. Analyses of human adhesion tissue confirm that similar genetic signatures are present in human disease. Our results highlight the deeply critical role that injured mesothelium plays in adhesion formation and investigates its pathophysiology cellularly and molecularly.

EXAMPLE 1

Materials and Methods
Adhesion Induction

Adhesion induction surgeries were done on wild type B6 (C57BL/6J (The Jackson Laboratory) mice aged 6-10 weeks. Mice were anesthetized by inhaled isoflurane until determined unconscious confirmed by toe-pinch test. The abdomen was disinfected with betadine and phosphate buffered saline (PBS). A left mid-clavicular incision was made in the skin running down the length of the mouse. A similar left-mid clavicular incision was made in the peritoneum running down the length of the peritoneum. The peritoneum was gently folded to the right and held down by a hemostat. A single, ischemic button was placed on the right half of the peritoneal wall by clamping a small (~5 mm diameter) piece of peritoneum and ligating the base with a 4-0 silk suture (Ethicon, 683G). Light abrasion on the button (24 times) and on the adjacent liver, cecum, and small and large bowels (7 times) was optionally performed (depending on the desired adhesion severity) with a surgical brush. Light brushing with fewer repetitions was performed to avoid pinpoint bleeding. The peritoneum was closed using 4-0 silk sutures and the skin was stapled closed (EZ Clips, 9 mm, Braintree Scientific Inc). Mice were allowed to recover on a heating pad and injected with 0.05-0.1 mg/kg of buprenorphine. Mice were followed closely and monitored daily for signs of morbidity for 7 days until euthanasia. Adhesed tissues were dissected, scored, and fixed in 2% paraformaldehyde overnight at 4 degrees.

Adhesion Scoring

In functional studies we assign a single score for an adhesion, based on the criteria detailed in the text above, taking into consideration both surface area contact and molecular makeup. However it should be noted that the amount of surface area contact does not always dictate molecular phenotype and vice versa, as the severity of the adhesion likely exists on a continuum represented by our discrete criteria described above. We have observed adhesion areas with high surface area contact (a score of 3 or 4) with little or no collagen or macrophage involvement (F4/80-). Conversely, we have also observed adhesion areas with low surface area contact (a score of 2) with high collagen and macrophage infiltration. In these cases we will score adhesions based on surface area contact or number of organs involved, as we predict this is a more significant indicator of clinical outcome.

Histology

Tissues were fixed in 2% paraformaldehyde overnight at four degree and were embedded and frozen in optimal cutting temperature compound O.C.T (Sakura) or embedded in paraffin. Frozen sections were cut at 10-12 um throughout the adhesed organs and saved for immunofluorescence. Paraffin sections were cut at 5 um and hematoxylin/eosin and Masson's trichome stains were performed via standard protocols.

Immunofluorescence

Immunofluorescence studies were performed on frozen sections. Frozen sections were thawed at room temperature for ten minutes and washed in PBS twice. Slides were blocked in 5% serum for 30 minutes at room temperature. Sections were subsequently stained with primary antibodies against PDPN (1:100, mouse monoclonal, Abcam), MSLN (1:200, rabbit monoclonal, ABBIOTEC), fibronectin (1:100, rabbit monoclonal, Abcam), F4/80 (1:100, rat monoclonal, Abcam), CD31 (1:100, rabbit monoclonal, Abcam), pan-collagen (1:100, rabbit polyclonal, Abcam), WT1 (1:100, rabbit polyclonal, Abcam), CD44 (1:100, rabbit polyclonal, Abcam), HIF1A (1:100, mouse monoclonal), and S100A4 (1:100, rabbit polyclonal, Abcam), overnight at 4 degrees, and washed three times in PBS. Slides were stained were incubated with secondary antibodies conjugated to Alex Fluor 488, 594, or 647 for one to two hours at room temperature. Stains were washed once with PBST and three times with PBS before nuclear staining with Hoechst 33342 (Life Technologies), for two minutes and mounted with Fluoromount G (Southern Biotech).

EdU Pulse-Chase

Following adhesion induction, mice were immediately injected subcutaneously with 0.025 mg of 5-ethynyl-2'-deoxyuridine (Life Technologies) in 90% PBS and 10% ethanol. Mice were traced for 7 days and euthanized. Adhesed tissues were dissected and fixed with 2% paraformaldehyde overnight, frozen in O.C.T (Sakura), and sectioned at 12 um. EdU positive cells were visualized with Click-iT EdU Imaging Kit (Life Technologies).

Flow Cytometry

A modified adhesion induction surgery was done according to previously described procedures on wild type C57BL/6J (The Jackson Laboratory). Two ischemic buttons were placed on each side of the peritoneum and no abrasion of the button or abdominal organs was done. Mice were allowed to recover for 6, 12, or 24 hours and euthanized. Ischemic buttons were dissected by cutting the base and placed in dissociation media (DMEM (Life Technologies, 10565-042), 50 mg/ml collagenase IV (Worthington Biochemical), 20 uM CaCl2). Buttons were homogenized using a single edge blade (Razor Blade Company), and incubated in dissociation media for 30 minutes at 37 C. The subsequent cell suspension was filtered through a 100 um filter and spun and washed with 2% fetal bovine serum (FBS) in PBS. Cells were treated with 1 ml of ACK lysis buffer (Life Technologies) for 5 minutes at 4 C and spun and washed. Cells were blocked with 1% goat serum (Life Technologies) for 10 minutes and stained with anti-PDPN (BioLegend, 8.1.1, 1:100), anti-LYVE-1 (eBioscience, ALY-7, 1:100), anti-CD31 (eBioscience, 390, 1:100), and anti-CD45 (BioLegend, 30-F11, 1:100) for 30 minutes at 4 C. Cells were spun down, filtered, and resuspended in 200u1 of 2% FBS in PBS. Cells were run through a FACSAria (BD Bioscences) and PDPN+LYVE1-CD31-CD45- cells were sorted directly into 750 ul of Trizol LS (Life Technologies).

RNA Sequencing and Analysis

Total RNA from sorted mesothelial population was isolated using Trizol (ThermoFisher) as per manufacturer's recommendation and was facilitated by addition of linear polyacrylamide (Sigma) as a carrier during RNA precipitation. Purified total RNA was treated with 4 units of RQ1 RNase-free DNase (Promega) at 37° C. for 1 hour to remove trace amounts of genomic DNA. The DNase-treated total RNA was cleaned-up using RNeasy micro kit (QIAGEN). 10-50 ng of total RNA was used as input for cDNA preparation and amplification using Ovation RNA-Seq System V2 (NuGEN). Amplified cDNA was sheared using Covaris S2 (Covaris) using the following settings: total volume 120 ml, duty cycle 10%, intensity 5, cycle/burst 100, total time 2 min. The sheared cDNA was cleaned up using Agencourt Ampure XP (Beckman Coulter) to obtain cDNA fragments>=400 base pairs (bp). 500 ng of sheared and size-selected cDNA were used as input for library preparation using NEBNext Ultra DNA Library Prep Kit for Illumina (New England BioLabs) as per manufacturer's recommendations. Resulting libraries (fragment distribution: 300-700 bp; peak 500-550 bp) were sequenced using HiSeq 4000 (Illumina) to obtain 2×150 base pair paired-end reads. The reads obtained were trimmed for base call quality and the presence of adapter sequences using Skewer (ref). High quality reads thus obtained were aligned to mouse genome using OLego (ref) and the levels of expressed mRNAs were estimated using cuffdiff2 (ref) and represented as fragments per kilo-base per million mapped reads (FPKM).

Antibody Treatments

Adhesions were induced in wild type B6 (C57BL/6J (The Jackson Laboratory) and allowed to recover for 7 days. 200 ug of monoclonal anti-MSLN (B35) antibody were administered via intraperitoneal injections at 7, 10, and 13 days post injection. 200 ug of monoclonal anti-CD47 (MIAP301) (BioXCell) were co-administered via intraperitoneal injections at the same frequency. Mice were euthanized 17 days after initial surgery and scored for adhesion severity. B35 anti-MSLN antibody was a gift from A. Miyajima.

In Vitro Mesothelial Culture

Wild type B6 (C57BL/6J (The Jackson Laboratory) were euthanized and the mesothelium was excised from the renal capsule and intestine. Excised mesothelium was cut into smaller fractions and placed into culture dishes pretreated with EmbryoMax 0.1% Gelatin Solution (EmdMillipore) for 30 minutes and cultured in Delbucco's Modified Eagle Medium (Life Technologies) with 10% fetal bovine serum, 1% penicillin/streptomycin and 1% non-essential amino acids at 37 degrees for 7 days. Mesothelial cells were co-cultured with macrophages (added to confluency) in normal conditions or in hypoxic conditions (1% O2 incubator or 100 uM CoCl2).

Preparation of Primary Bone-marrow Derived Macrophages (BMDMs)

To prepare primary BMDMs, BALB/c mice were humanely euthanized, and disinfected with 70% ethanol. An incision was made along the legs, and the muscle removed from the bones. The femur and tibia were removed from the body, and rinsed in PBS. The bones were flushed with a 6 mL syringe and 23 gauge needle, and the marrow resuspended in 10 mL RPMI. The suspension was centrifuged 5 minutes, 1200 rpm, and the pellet resuspended in 5 mL ACK lysis buffer (Invitrogen) for 5 minutes to remove blood cells. The suspension was filtered over a 70 µm Falcon cell strainer, and centrifuged again. The pellet was resuspended in 40 mL of macrophage media (RPMI+10% FBS+10% penicillin/streptomycin+10 ng/mL MCSF), and plated on four 10 cm petri dishes. On day 4, the macrophage media was replaced. On day 7, the macrophages were lifted from the dish and used.

Small Molecule Inhibitor Treatments

Adhesion induction surgeries were performed on 4-8 week old wild type B6 (C57BL/6J (The Jackson Laboratory) as previously described. 200 mg/kg of cryptotanshinone (Sigma Aldrich), 2 mg/kg of FM19G11 (Sigma Aldrich), 10 ug/kg or 20 ug/kg of echinomycin (Sigma Aldrich), or 25 mg/kg of PX12 (Sigma Aldrich) immediately after injury, 4 hours after injury, and every 24 hours subsequently for 7 days.

Parabiosis

Parabiosis surgeries were done on age matched (4-6 week old) female wild type B6 (C57BL/6J (The Jackson Laboratory) and C57BL/Ka Rosa26 mRFP1 mice. Mice to undergo parabiosis were housed together in a single cage for 10 days prior to surgery. Mice were anesthetized by inhaled isoflurane until determined unconscious confirmed by toe-pinch test. The sides of the mice were shaved and cleaned with 70% ethanol and betadine. Mice were laid next to each other and incisions from elbow to knee were made on adjacent sides. The elbow and knee joints were ligated using 4-0 sutures (Ethicon) and the loose skin from adjacent mice was stapled together. Mice were allowed to recover on a heating pad and injected with 0.05-0.1 mg/kg of buprenorphine. Mice were followed closely and monitored daily for signs of morbidity for 14 days. Staples were removed following 14 days and mice were bled retro-orbitally to assay for chimerism.

Results

To identify an adhesion model with consistent adhesion severity and location we analyzed current published rodent models that involved intraperitoneal (I.P.) injections of inflammatory chemicals, rough abrasion of the cecum and peritoneum using a surgical brush, sandpaper, or a similar instrument (Chung, 2002; Wei et al., 2015), cauterization of the peritoneum and abdominal organs (Kosaka, Yoshimoto, Yoshimoto, Fujimoto, & Nakanishi, 2008; T. Suzuki et al., 2015), and or placement of ischemic buttons in the peritoneal wall (Cassidy, Sherburne, Heydrick, & Stucchi, 2015). Our final model must be able to robustly predict the locations where adhesions will form so the cells of origins that initiate and contribute to the adhesion can be readily identified and isolated during adhesion development. We found that the use of chemical methods or general abrasion made it difficult to control the locations and severities of abdominal adhesions, even with a localized abrasion to organ surfaces (on the peritoneum, cecum, liver). The locations of adhesion formations were often unpredictable, likely due to peritoneal inflammation. Cauterization led to high morbidity and inconsistent adhesion formations as well.

Out of the established models, we found that placing a single ischemic button on the right half of the peritoneal wall (see 'Materials and Methods') resulted in adhesions between the button and liver or intestine, with little or no morbidities. Optionally, we found that by applying a gentle abrasion of the button and of the adjacent abdominal organs followed, we would able to control the severity of the adhesion. Using this adhesion protocol we were able to consistently control the site of adhesions and therefore predict the location of the adhesion forming cells, and their severity to explore in more detail the transition of surface mesothelium during the progression of the disease.

Following surgery, mice were allowed to recover and euthanized 30 minutes, 1 h, 2 h, 4 h, 24 h, 72 h, and 7 days post induction. All ischemic buttons with ectopic adhesions that developed were dissected, fixed, and stained with haematoxylin and eosin (H&E) or with Podoplanin (PDPN) and Mesothelin (MSLN), mesothelium surface receptor markers (Rinkevich et al., 2012). An intact cellular layer was clearly visible on the ischemic button with and without abrasion at all time points post surgery (FIG. 1A, 1B) indicating that the mesothelium is not denudated, nor does it retract following mechanical stress or injury. Four hours post surgery, the mesothelium underwent cellular proliferation, and showed thickening 24 h hours after induction (FIG. 1B), becoming a multi-cellular layer. Cell proliferation was localized to the site of injury, as undamaged mesothelium both adjacent to the button exhibited normal single cell layer morphology. Significant adhesion formation developed locally at 7 days post induction, with the adhesion tissue staining strongly for both PDPN and MSLN (FIG. 1C), suggesting that adhesion foci are derived from the underlying mesothelium and comprised of mesothelial cells.

To confirm that adhesion foci are derived from surface mesothelium and not circulating cells, we performed parabiosis studies on C57BL/6J mice and C57BL/Ka Rosa26 mRFP1 mice, constitutively expressing red fluorescent protein (RFP)(Ueno & Weissman, 2006). The vasculature of aged matched (4-6 week old) female mice was connected (see "Materials and Methods") and after 14 days, parabiotic mice were confirmed to have achieved blood chimerism. Adhesions were then induced in non-colored wild type C57BL/6J mice of the parabionts and after 7 days were assayed for adhesion formation. Parabiotic adhesions were sectioned and stained with PDPN to confirm mesothelial cell contribution. PDPN+ cells were observed to be visible throughout all adhesion sites and were found to be non-colored, indicating that mesothelial cells contributing to the adhesion are derived from a local source instead of circulating cells (FIG. 1D). RFP+ cells were visible and scattered throughout the adhesion site and many RFP+ cells also stained positive for F4/80, indicating that macrophages derived from circulating monocytes, infiltrate the adhesion site.

We also performed 5-ethynyl-2'-deoxyuridine (EdU) pulse chase studies following adhesion induction to assay for cell proliferation. Mice were injected with 0.025 mg of EdU intraperitoneally after adhesion induction and allowed to recover for 7 days until they were euthanized and their adhesions dissected, sectioned, and stained for EdU, PDPN, and MSLN. Mesothelial cells (defined as PDPN$^+$or MSLN$^+$) cells were counted in multiple (n=20) high power (0.75 mm×1 mm fields) in control mice (undergoing no adhesion induction), and mice (n=16) following adhesion induction. There were significantly greater numbers of mesothelial cells in areas of adhesion when compared to control mice, indicating increased number of mesothelial cells in adhesions (FIG. 1E, 1F). To assess for mesothelial proliferation, the number of double positive EdU$^+$MSLN$^+$ or EdU$^+$PDPN$^+$ cells were counted in a 0.75 mm×1 mm field (n=20). We found a large increase of double positive cells in adhesion areas over control areas, indicating that the adhesion is largely due to the expansions of preexisting mesothelial cells at sites of injury (FIG. 1E, 1F).

Figure 2B:
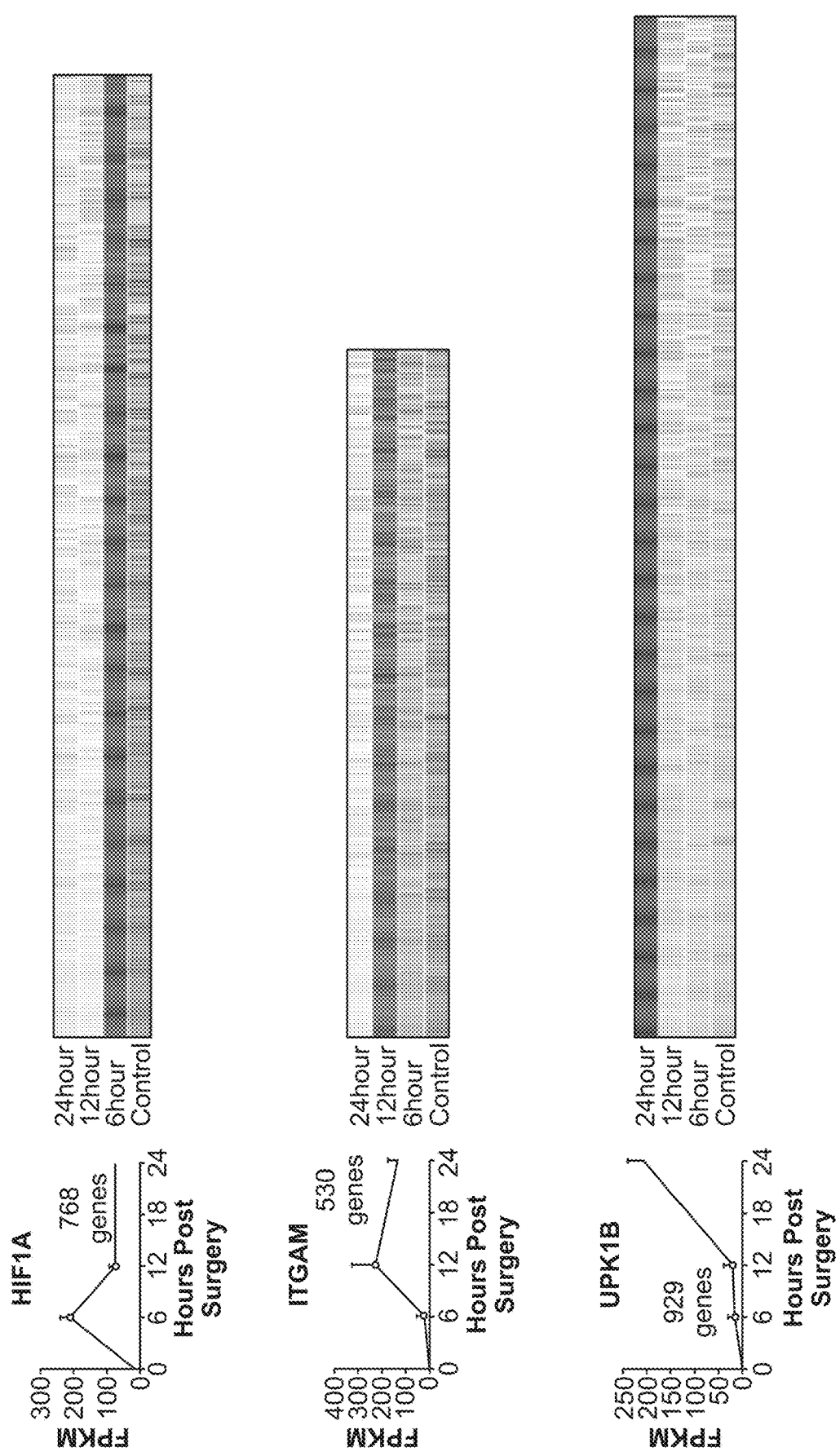

To better understand the changes in the transcriptional landscape in mesothelial cells that lead to adhesion formation, we isolated mesothelial cells from the induction site at 6, 12, and 24 hours following adhesion induction by employing fluorescent activated cell sorting (FACS) with the following mesothelium cell surface phenotype: PDPN$^+$ LYVE1$^-$CD31$^-$CD45$^-$ (FIG. 2A). In order to obtain adequate amounts of mesothelial cells, four buttons were placed onto single C57BL/6J mice (two on each side of the peritoneal wall). Five mice (20 buttons) were taken for a single triplicate, and three cohorts of mice were sacrificed 6, 12, or 24 hours post injury. Peritoneal mesothelial cells were isolated by FACS from mice that did not undergo surgery and were used as a control (t=0) reference point for transcriptional changes associated with the induction of an adhesion program. RNA was isolated from pooled cells and sequenced according to standard procedures (see "Materials and Methods"). Differentially expressed genes were clustered based on expression patterns across the 24 hour time course and run through gene set enrichment analyses (see "Materials and Methods") to elucidate the global transcriptomic landscape that occurs in the first 24 hours of adhesion progression (FIG. 2B,C,D).

We found that differentially expressed genes broadly clustered into six main expression patterns, peaking or dipping at 6, 12, and 24 hours (FIG. 2B), corresponding to what we believe are two main events in adhesion pathogenesis: initiation and progression. Early genes, which show maximal or minimal expression after 6 hours, are likely regulators of the adhesion process and initiation formation. Intermediate genes, peaking or dipping at 12 hours, are likely responding to early genes can potentially lead to adhesion progression. Late genes, increasing or decreasing at 24 hours, are likely the genes that control adhesion progression.

Figure 2C:
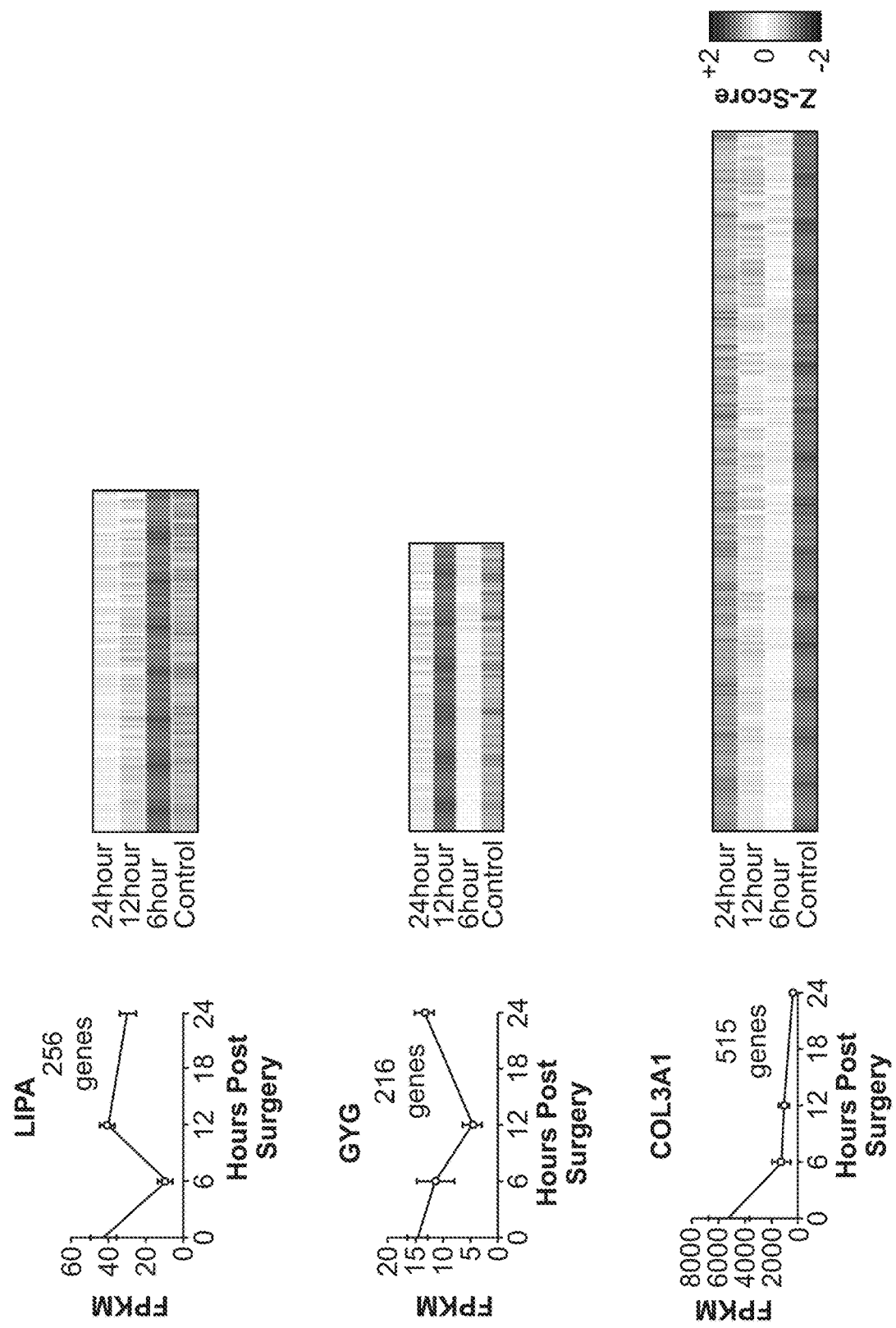

Fold changes of transcripts after 6, 12, and 24 hours were also calculated and plotted against the entirety of the genome (FIG. 2C). Significantly upregulated or downregulated genes were calculated based on a q<0.05 threshold, plotted against gene identity and ordered by significance in fold change. Strikingly, we found that within 24 hours, approximately 8000 genes were significantly differentially expressed in the mesothelium after injury. The amount of genes that are significantly upregulated and downregulated during our time course rival changes found between terminally differentiated macrophages and B-cells, approximately XXXX, (unpublished data). This indicates that injured mesothelial cells undergo a complete transformation in the first 24 hours following injury, and hints at the unexplored diversity that exists in the mesothelium.

Figure 2D:
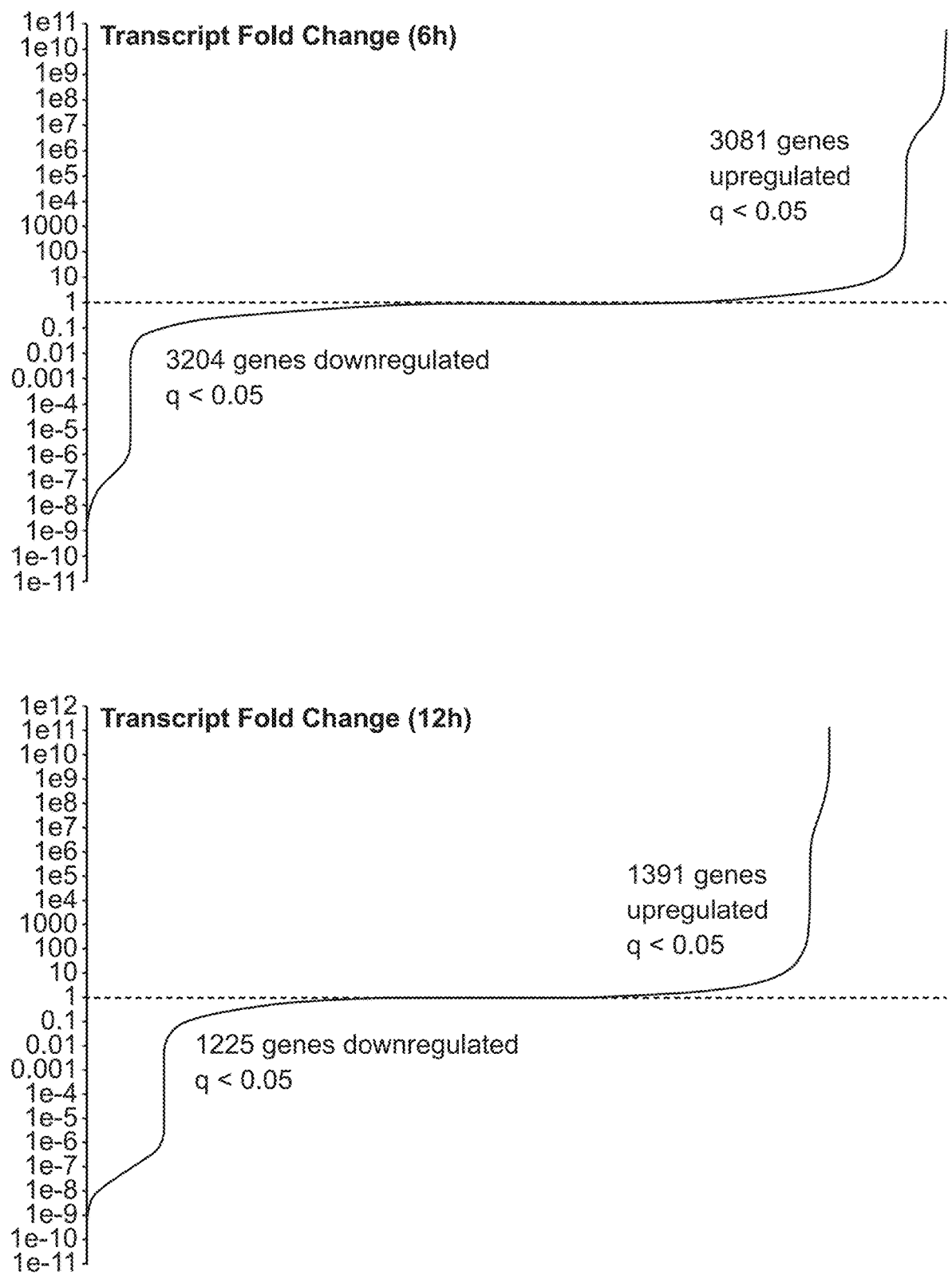

Analysis of genesets enrichment using GO term analysis (FIG. 2D) shows within the first six hours of induction early genes associated with angiogenesis and hypoxia response are upregulated in mesothelial cells. Hallmark mediators of the inflammatory response were significantly upregulated over the entire 24 hour time course, including chemokine and chemotaxis activity, cytokine secretion, and the NF kappa B pathway (FIG. 2D). Fundamental cellular processes such as proliferation are upregulated over a course of 24 hours, corroborating our pulse-chase experiments.

Interestingly, genesets relating to the extracellular region and collagen organization were downregulated across the 24 hour time course following adhesion induction. These genesets include the specific genes fibronectin 1 (FN1), and various collagens including COL1A1, COL1A2, COL3A1, (FIG. 2D) indicating major transcriptional rearrangements take place during the early stages of mesothelial injury.

Classical developmental pathways were also decreased over this time window; Wnt, Hedgehog, BMP, and Hippo signaling pathways were all found to be downregulated in the first day after adhesion induction, though the significance of this has yet to be explored. Finally, the TGF family, a pathway thought to contribute significantly to adhesion formation and inflammation in general, was found to be downregulated in the mesothelium over 24 hours (FIG. 2D), indicating that an upregulation in TGF signaling is not occurring in mesothelial cells in vivo.

Finally, we performed direct analysis of the behavior of specific genes. Interestingly, many specific markers expressed by mesothelium during embryonic development were upregulated after injury, specifically mesothelin (MSLN), uroplakin1B (UPK1B), and Wilm's Tumor 1 (WT1), all of which peak at 24 hours (FIG. 2E), suggesting they may regulate the later stages of adhesion formation. Re-expression of embryonic genes after injury is not uncommon but hints at a proliferative phenotype. We also found that hallmark fibroblast genes, specifically S100A4, also known as Fibroblast specific protein 1 (FSP1), and smooth muscle actin (ACTA2) are also upregulated after injury, suggesting that the mesothelium differentiates into a more fibroblast like phenotype after injury. Finally, we noticed that adhesion molecules are upregulated, indicating that adhesion and migration may play an important role in adhesion formation.

Figure 2E:
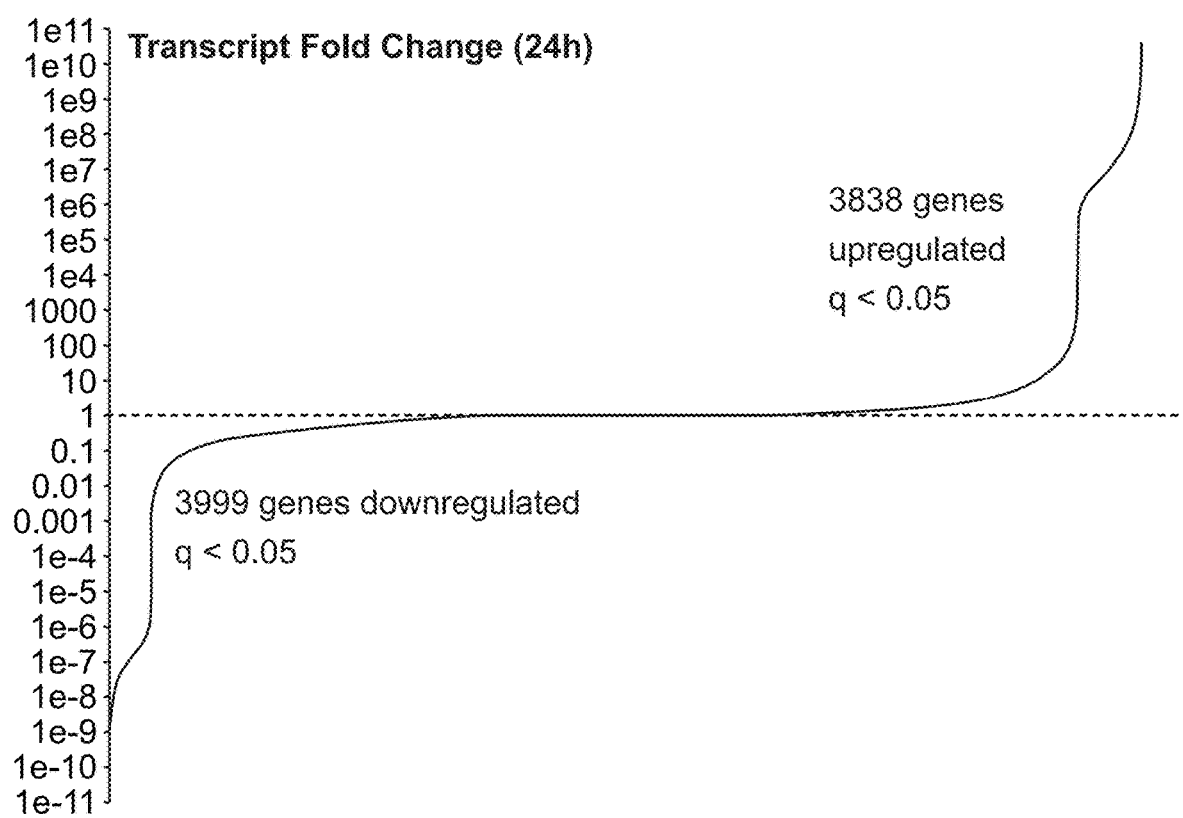

To identify initiating regulators of the adhesion program we looked for transcription factors that peaked within the first 6 hours of adhesion induction and that remained constant or decreased shortly after. The gene expression profile for hypoxia inducible factor 1 alpha (HIF1A) matched this trend (FIG. 2B, 2E).

Figure 2F:
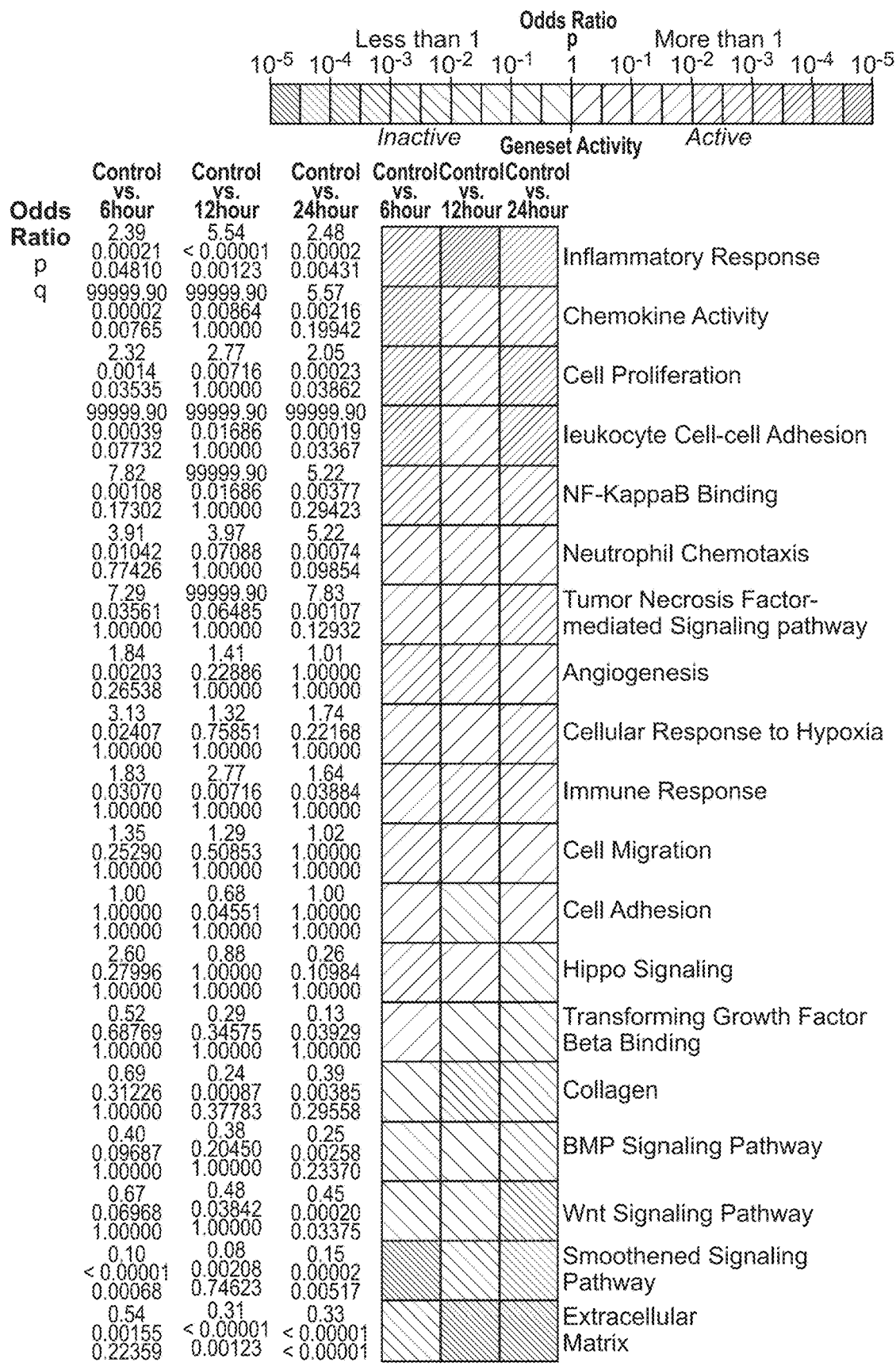
Figure 2G:
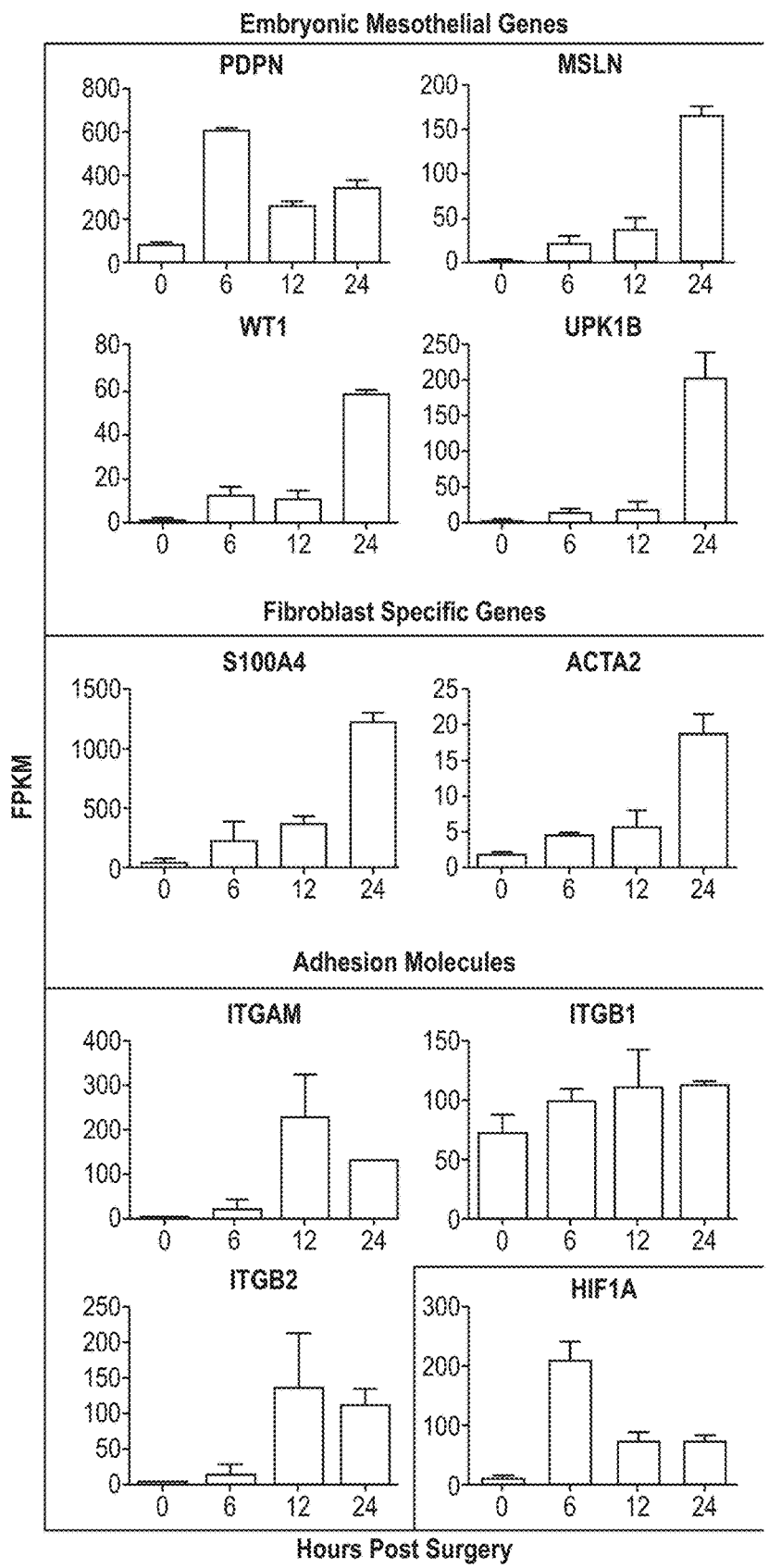
Figure 2H:
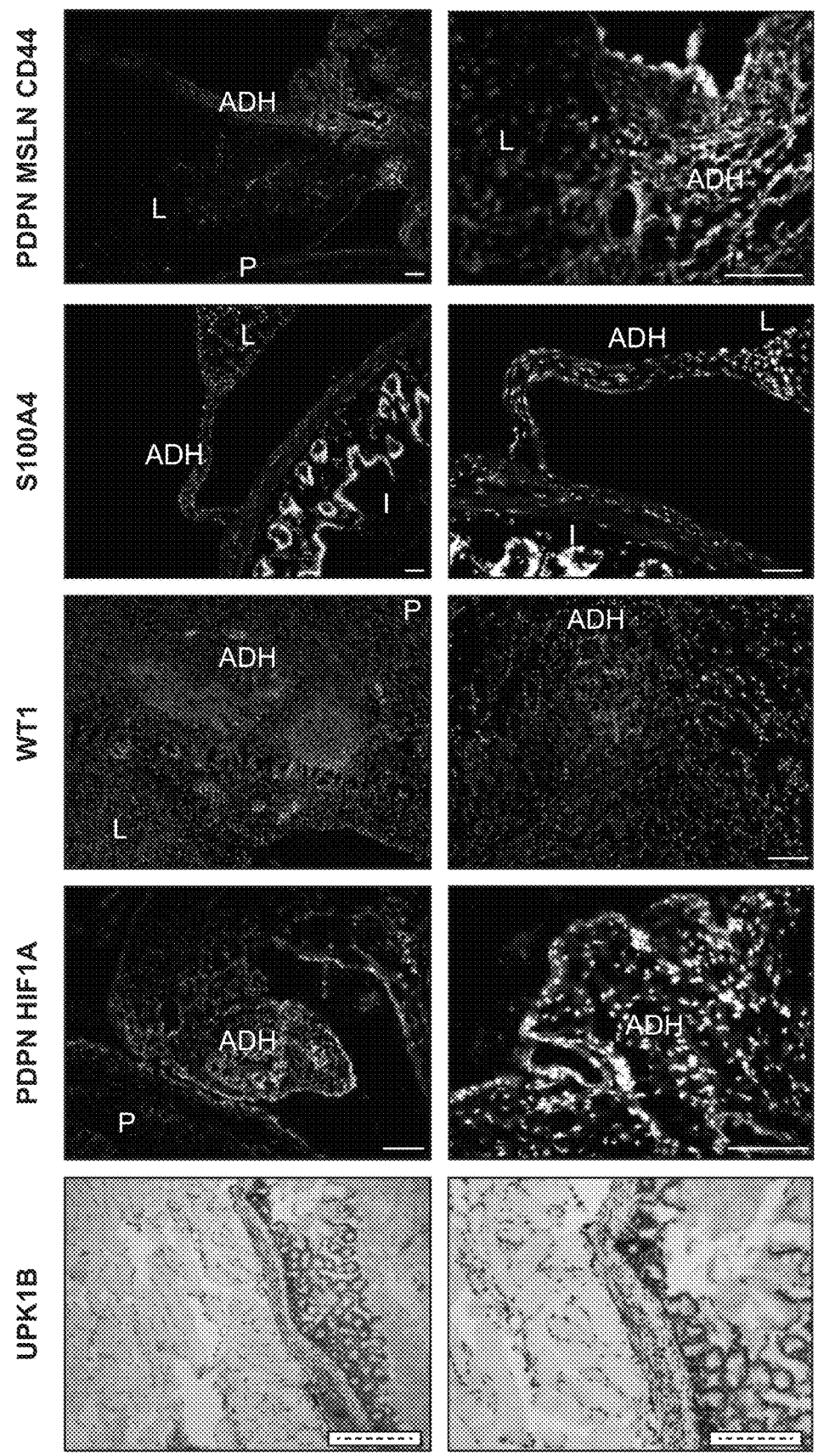

To validate our RNA sequencing screen, we induced adhesions in wild type C57BL/6J mice as described previously, and immunostained the subsequent adhesions 7 days after surgery for our gene targets (FIG. 2F). We observed strong expression of many of our targets and immunofluorescence and in situ hybridization analysis demonstrate the specificity of our approach to the surface mesothelium and its derived adhesion tissue. Some targets, such as PDPN, MSLN, and HIF1A, are expressed throughout the adhesion tissue, whereas WT1 activated within a subpopulation of the adhesion foci indicating heterogeneity within the mesothelium and the adhesion.

In order to functionally interrogate these targets, we first required a method to evaluate the severity of an adhesion. Previous studies have characterized adhesions by focusing on the strength (mechanical difficulty in separating adhesed organs) and or the number of organs adhesed in order to score adhesion severity (Dinarvand, Hassanian, Weiler, & Rezaie, 2015; Kosaka et al., 2008; Wang et al., 2014).

Our standard scheme for scoring adhesions took into consideration both the extent of the adhesed surface area, as well as the molecular makeup of the adhesion, providing a detailed cellular and molecular guide to score adhesion severity, with severity of the adhesion exhibiting a continuum of our discrete criteria described bellow. Adhesions were induced in wild type C57BL/6J mice using the method described above, with different intensity and scope of abrasions to induce a range of adhesion severity. These mice were allowed to recover for seven days before their adhesions were scored.

Figure 3A:
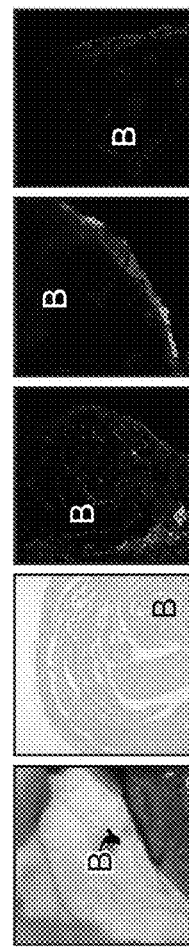
FIG. 3A-3F.
Figure 3B:
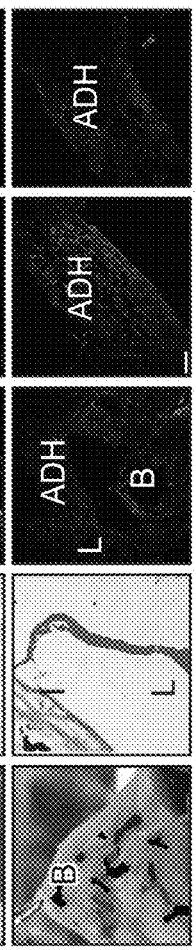

In our scheme, an adhesion with a score of 0 has no adhesion between two areas, with limited mesothelial thickening on the button (FIG. 3A). The area stains positive for MSLN and fibronectin (FIG. 3A). Mice with an adhesion score of 0 had no signs of morbidity and survived the 7 day recovery period (n=25). An adhesion score of 1 indicated a "string" adhesion, connecting the two adhesed areas with a light fibrous bridge (FIG. 3B). The string and surrounding areas were immunopositive for MSLN and fibronectin (FIG. 3B). Most mice with an adhesion score of 1 had no signs of morbidity and survived the 7 day recovery period (n=11).

Figure 3C:
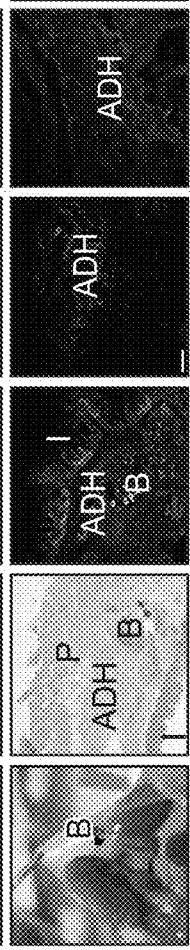
Figure 3D:
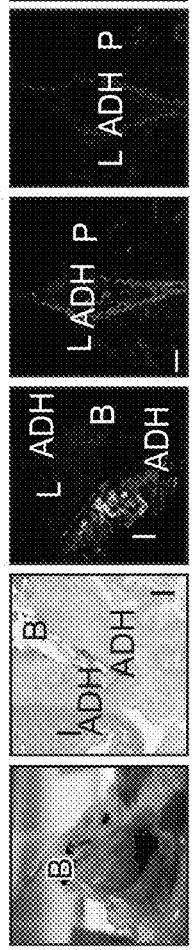
Figure 3E:
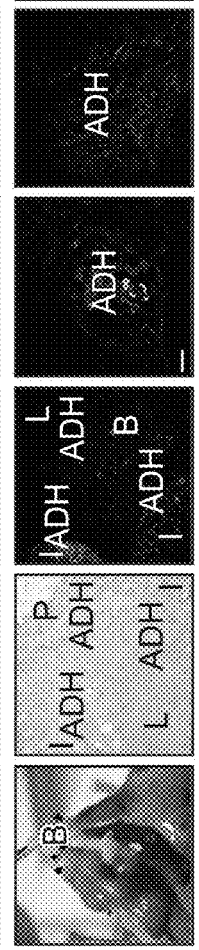
Figure 3F:

All adhesions with scores of 2 or above involve a single direct contact between two tissues. The adhesion contact itself was light, and usually involved contact between the peritoneum and an abdominal organ (FIG. 3C). The adhesion in between the two adhesed areas stained positive for MSLN, fibronectin, and F4/80, suggesting some macrophage infiltration has occurred (FIG. 3C). Most mice with an adhesion score of 2 had no signs of morbidity and survived the 7 day recovery period (n=12). An adhesion score of 3 was characterized by direct, continuous contact of three areas, usually between the peritoneum and two abdominal organs or two distinct, non-continuous areas of a single organ (FIG. 3D). The adhesed area stained positive for MSLN, fibronectin, F4/80, pan collagen, and CD31 (FIG. 3D). Most mice with an adhesion score of 3 had little signs of morbidity and survived the 7 day recovery period (n=9). An adhesion score of 4 included direct and continuous contact of four or more areas, usually between the peritoneum and three abdominal organs, or multiple separate areas of one or two organs (FIG. 3E). The adhesed area stained positive for MSLN, fibronectin, F4/80, pan collagen, and CD31 (FIG. 3E). Most mice with an adhesion score of 4 showed little signs of morbidity and survived the 7 day recovery period (n=14). An adhesion score of 5 was characterized as full compaction/encapsulation of the abdominal organs. Most organs were adhesed to the peritoneum as well as to each other as a single, rigid mass (FIG. 3F). The adhesed areas stained positive for MSLN, fibronectin, F4/80, collagen, and CD31 (FIG. 3F). Most mice with an adhesion score of 5 were visibly morbid with low survival rates at 7 day post injury (n=5).

Figure 5A:
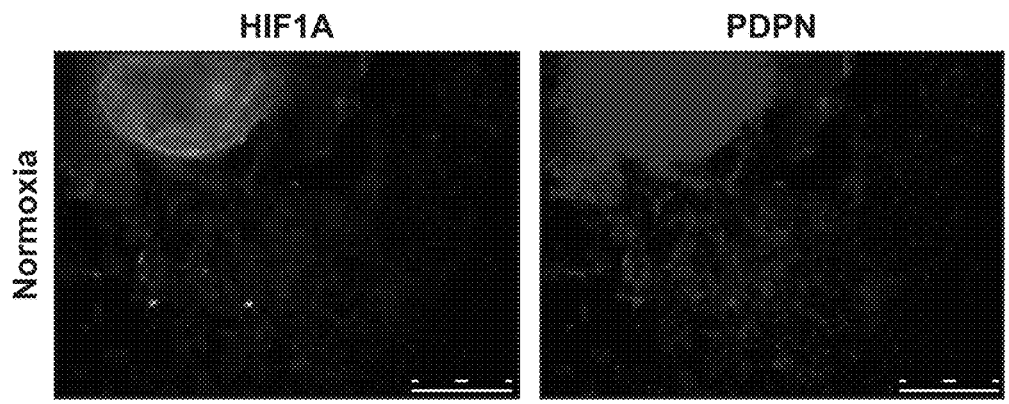
FIG. 5A-5F: Knockdown of HIF1α is sufficient for adhesion prevention.
Figure 5B:
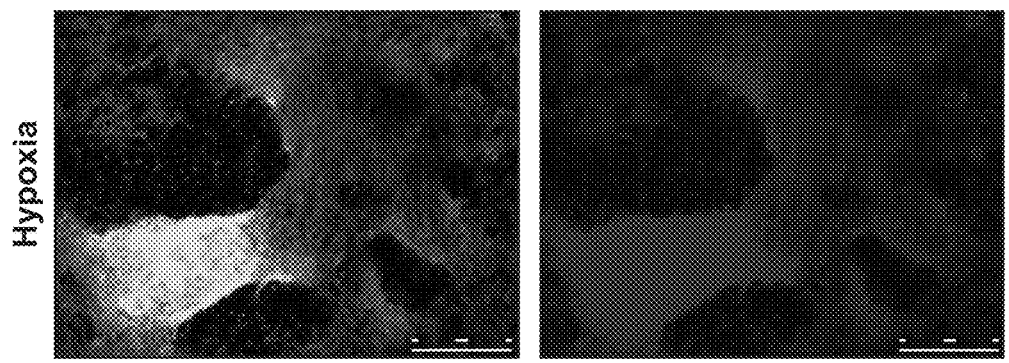
Figure 7:
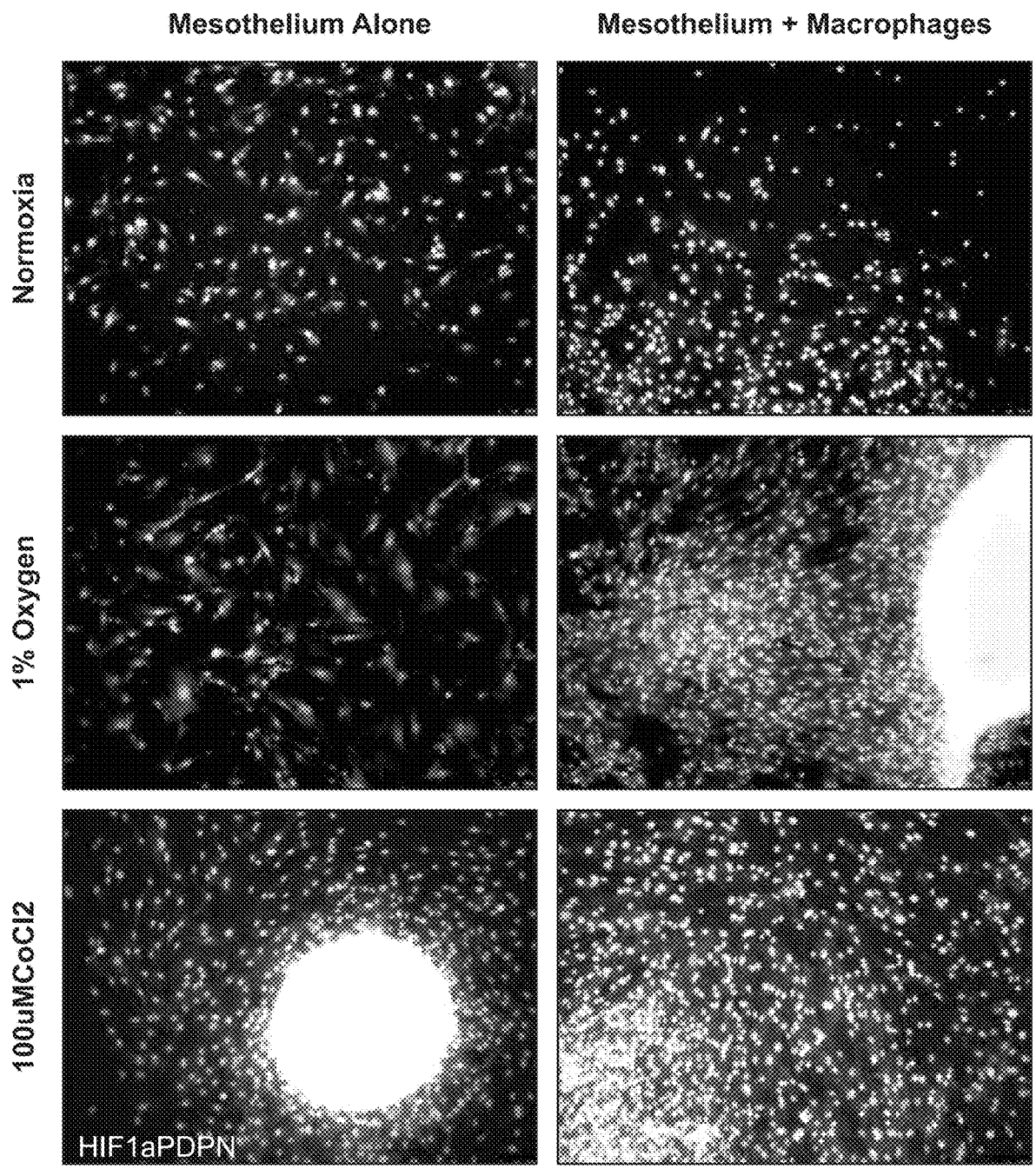
FIG. 7: Mesothelial in vitro culture assay. Mesothelial explanted cultures with and without macrophages in different oxygen conditions. Co-cultures were placed in normal oxygen conditions, 5% oxygen incubator, and in 100 uM $CoCl_2$.

To explore preventative routes we focused our initial attention on the HIF1A transcription factor, as it is significantly increased in transcript abundance at 6 hours post injury. First, we analyzed the potential effects HIF1A exerts on surface mesothelium in vitro. Primary mesothelial cells were removed from the renal capsule and intestine and transplanted on cultured wells as previously described (Rinkevich et al., 2012). After 7 days mesothelial cells emerged from their tissue explant and expanded on the culture dish. Cultured mesothelial cells were incubated in low oxygen conditions (5% $O_2$ or in the presence of 100 uM $CoCl_2$) for three days. Surprisingly, little morphological difference was seen between the hypoxic and normal mesothelium (FIG. 7). In contrast, 7-day-old mesothelial explants that were co-cultured with macrophages derived from the same mouse showed a striking morphological response (FIG. 5A, B) becoming highly dense and fibrocytic, and stained positive for PDPN and HIF1A. Though the fibrocytic phenotype was concentrated near the explant, mesothelial cells derived from adjacent explants would often grow towards each other.

Figure 5C:
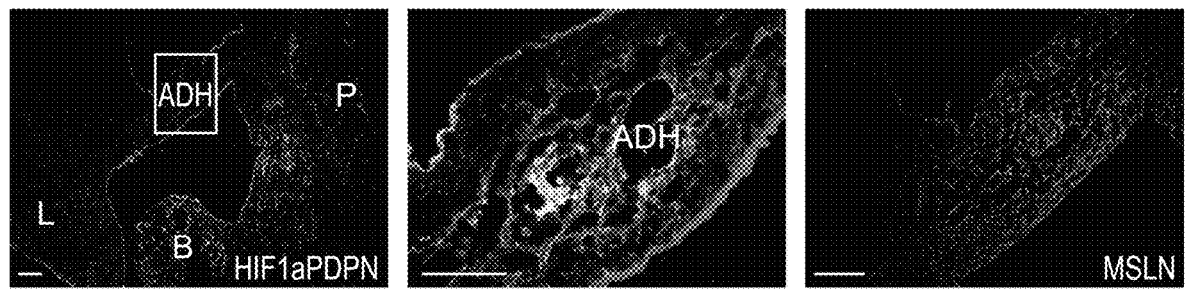
Figure 5D:
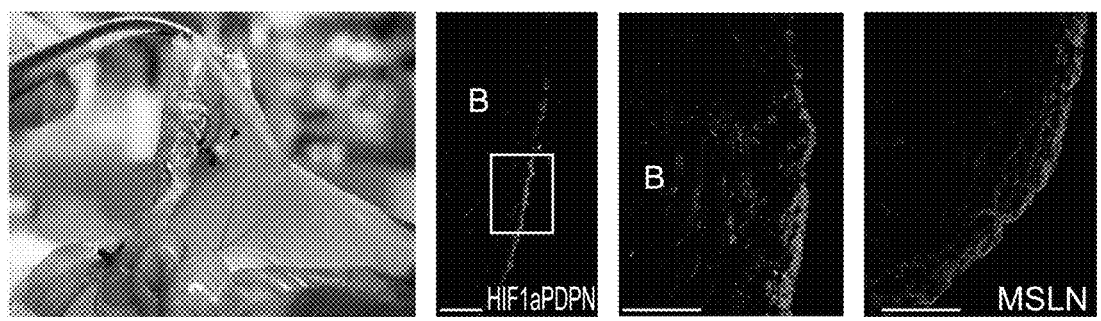
Figure 5E:
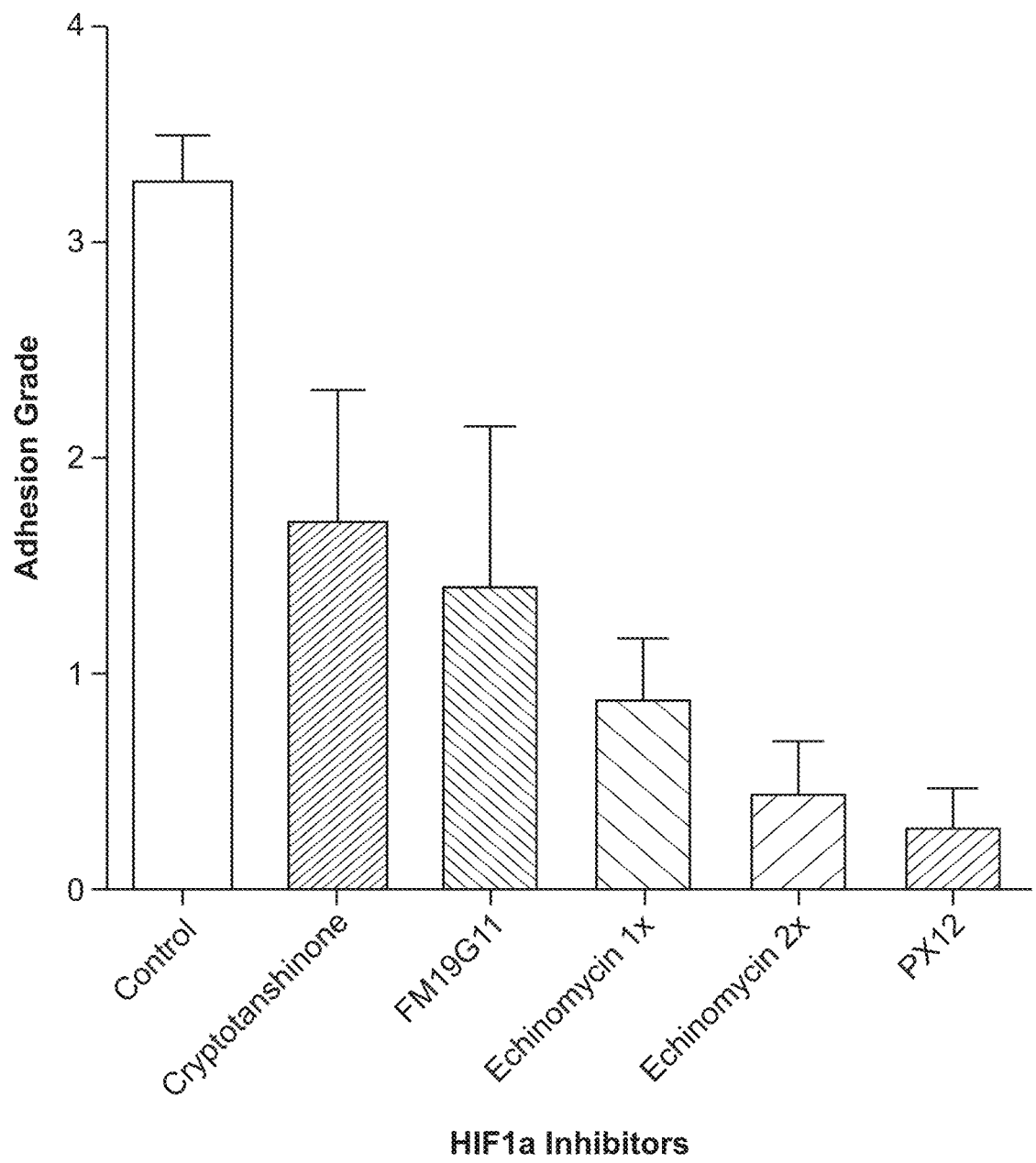

To explore whether inhibiting the HIF1A pathway in vivo can prevent adhesion formation, we treated mice that had undergone adhesion induction with small molecular inhibitors against HIF1A or its immediate downstream cascade. We chose cryptotanshinone (Sigma Aldrich) which inhibits HIF1A activation (Dat et al., 2007), FM19G11 (Sigma Aldrich) which represses the targets of the alpha subunits (Moreno-Manzano et al., 2010), echinomycin (Sigma Aldrich) which blocks HIF1A DNA binding (Kong et al., 2005), and PX-12 (Sigma Aldrich) which blocks HIF1A transcriptional activity (Kim, Coon, Baker, & Powis, 2011). Wild type C57BL/6J mice underwent adhesion induction and were injected with (200 mg/kg) of cryptotanshinone or (2 mg/kg) of FM19G11 or (10 ug/kg or 20 ug/kg) of echinomycin or (25 mg/kg) of PX12 immediately after injury, 4 hours after injury, and every 24 hours subsequently for 7 days. Mice were euthanized after 7 days and their adhesions were imaged and scored. Control adhesions were positive for PDPN, MSLN and HIF1A (FIG. 5C) whereas mesothelium surrounding the buttons in mice treated with echinomycin or PX12 stained with only MSLN and PDPN (FIG. 5D). More importantly, adhesions in these areas were significantly reduced (FIG. 5E), with a majority of the mice treated with PX12 (n=5) or with echinomycin (n=15) showing no adhesions (score 0).

To broadly determine the causative transcriptional changes in injured mesothelial cells downstream of HIF1A inhibition, we treated 10 wild type C57BL/6J mice with (20 ug/kg) of echinomycin prior to and immediately following adhesion induction via placement of four ischemic buttons. Using a similar method as outlined above, we isolated the damaged mesothelium from buttons, sorted and isolated their RNA for sequencing.

Figure 8:
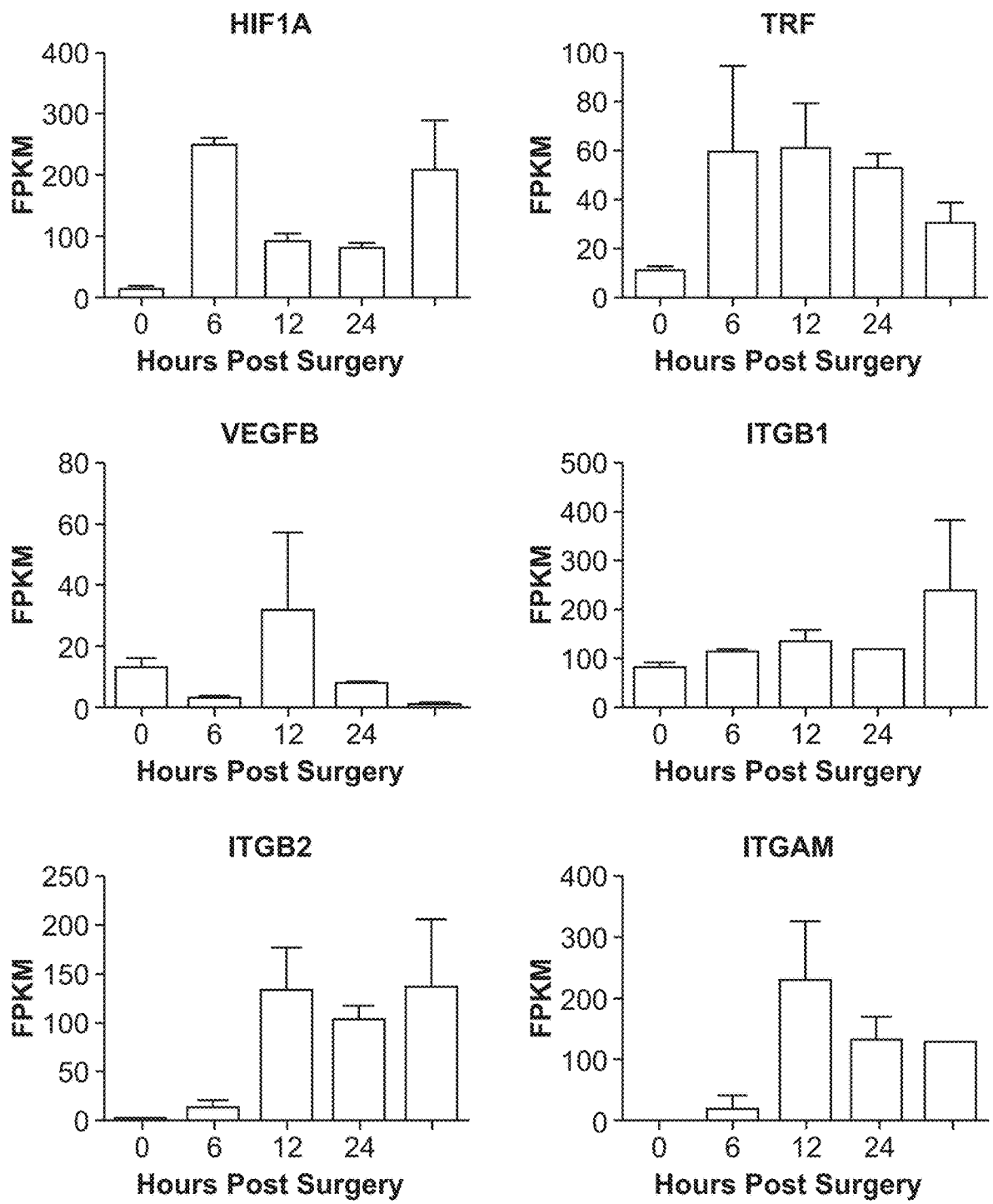
FIG. 8: HIF1A and mesothelial gene targets after HIF1A knockdown. Expression values from a RNA sequencing screen of HIF1A and mesothelial targets genes were taken over a 24 hour time course and compared to samples treated with 20 ug/kg echinomycin.

We first confirmed that known HIF1A targets VEGFb and transferrin (TRF) were found to be downregulated after echinomycin treatment (FIG. 8). After applying similar analyses, we found that over 200 genes that were normally upregulated along our initial 24 hour time course were decreased with HIF1A inhibition. Conversely, over 600 genes showed little or decreased expression during the 24 hour time course were upregulated by HIF1A inhibition (FIG. 5F).

Many of our initial target genes (FIG. 2E) were unaffected by echinomycin treatment. Specifically ITGAM, ITGB1, and ITGB2 showed little difference in gene expression after HIF1A inhibition (FIG. 8). Interestingly, PDPN, MSLN, and S100A4, all increased in expression after echinomycin treatment (FIG. 5F).

Figure 5F:
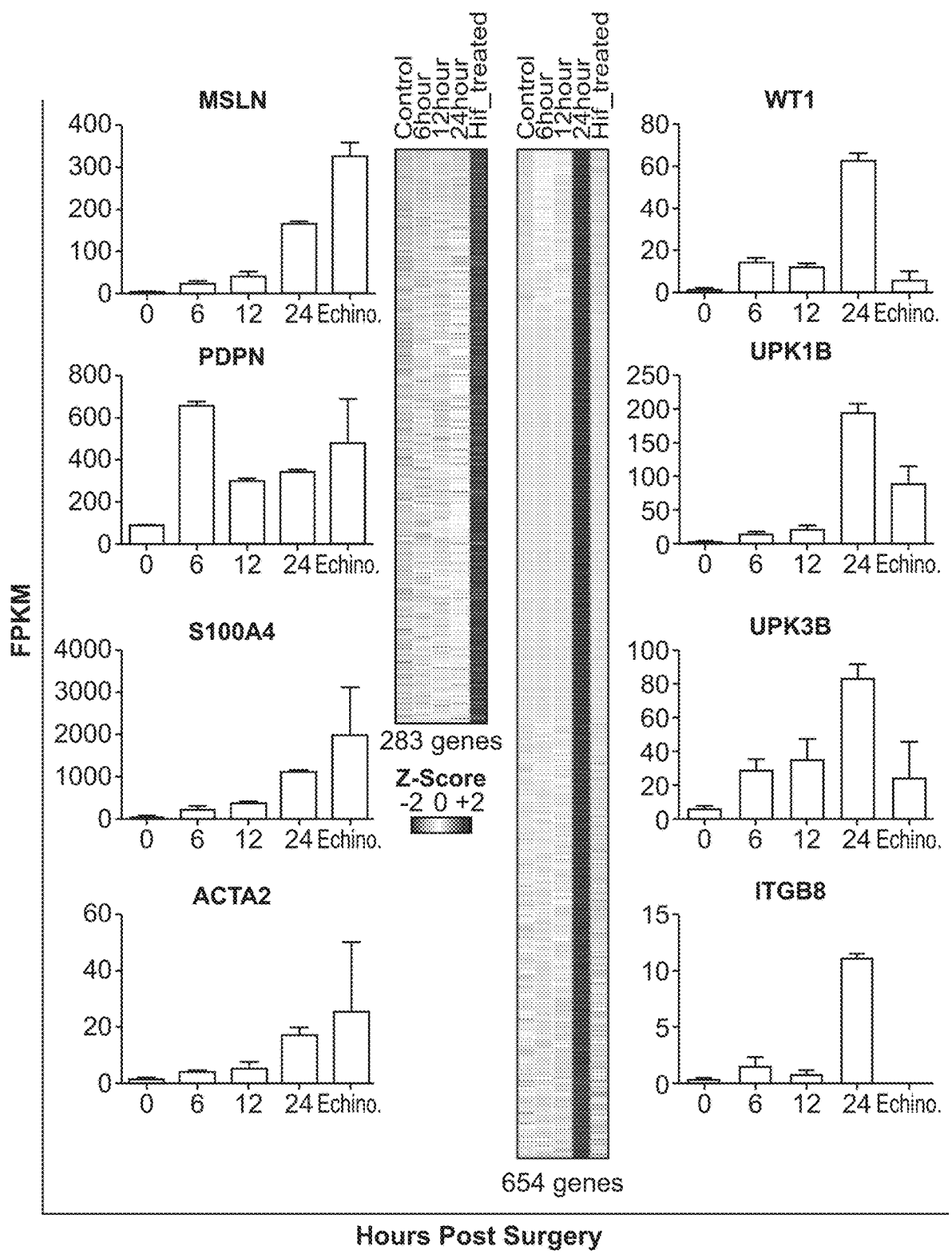

However, from our initial target screen, UPK1B and WT1 were found to be HIF1A dependent, as their expression levels dropped significantly following echinomycin treatment (FIG. 5F). These results therefore suggest that the embryonic mesothelial genes WT1 and UPK1B are targets of HIF1A during adhesion initiation and begin to draw a hypoxia dependent pathway to initiate adhesion formation.

Many studies have been done to prevent adhesion formation or to diminish adhesions once they have been established. Our RNA sequencing screen provided us with potential targets for both preventative and post-formation treatments. We previously observed that adhesions are highly cellular, and therefore hypothesized that clearance of adhesion tissue may be induced via elimination of these cells using an immunotherapy approach involving specific targeted antibodies. MSLN is an embryonic mesothelial surface molecule that has very limited expression in the adult, but is re-expressed upon mesothelial injury and adhesion induction, making it an ideal candidate for targeting. Mouse monoclonal anti-MSLN antibodies were found to bind to injured sites immediately after adhesion induction and antibody injection (FIG. 4A).

We and others have recently shown that targeting immune adjuvants in addition to primary targets greatly increases the efficacy of tumor clearance. Specifically, CD47 is a surface receptor that is highly upregulated on a spectrum of tumors and acts as a "don't eat me signal," inhibiting phagocytosis by binding to SIRP1α, its ligand on macrophages. Inhibition of this interaction by blocking either CD47 or SIRP1α, in addition to administration of tumor specific monoclonal antibodies, has been shown to greatly decrease tumor burden and increase survival (Chao et al., 2010; Chao, Weissman, & Majeti, 2012; Jaiswal et al., 2009; Tseng et al., 2013). We observed high CD47 expression in the mesothelium prior to and 24 hours following adhesion induction (FIG. 4B), indicating that a similar regimen may help to induce adhesion clearance.

Figure 4F:
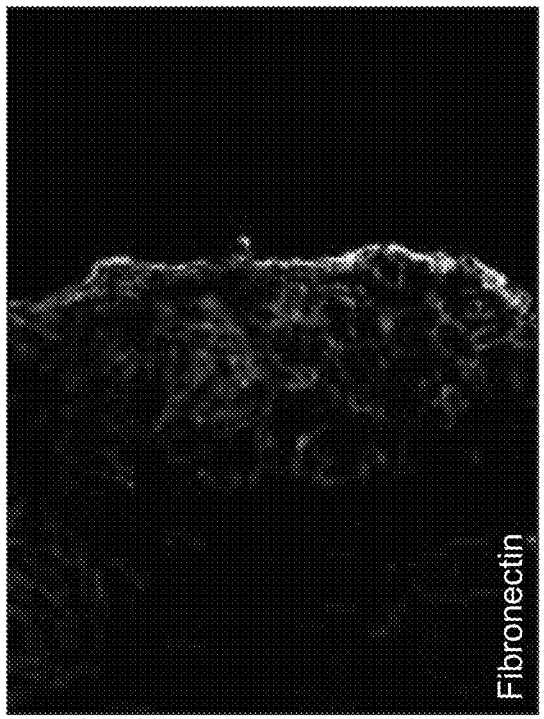
Figure 4F:
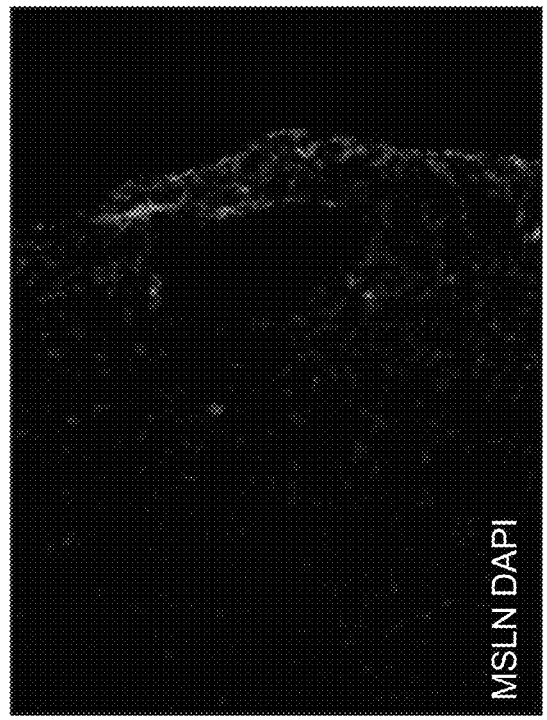
Figure 4F:
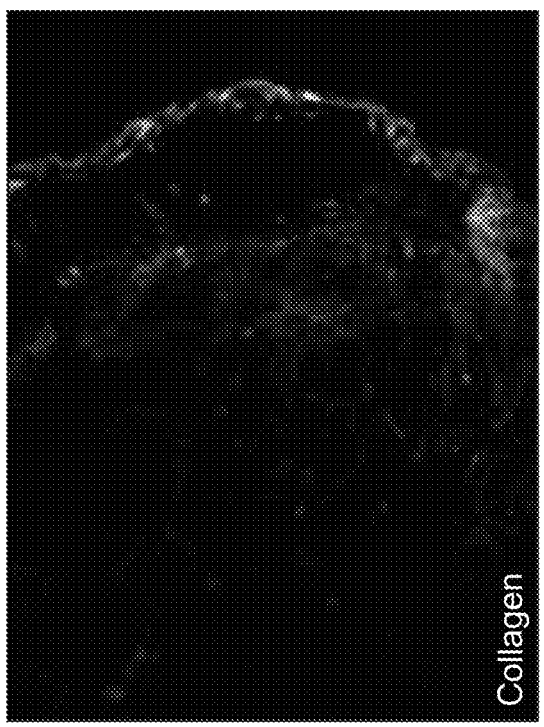
Figure 4F:
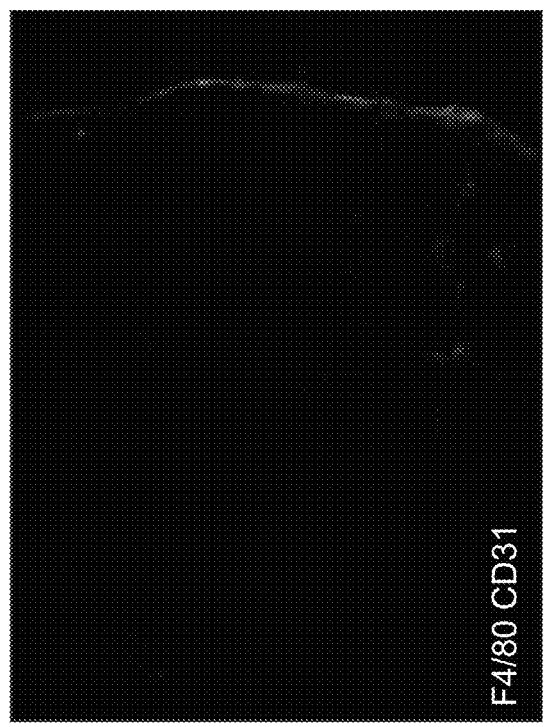

To explore whether MSLN antibody binding could initiate adhesion clearance, we induced adhesions in wild type C57BL/6J mice and allowed mice to recover for 7 days. We then administered 200 ug of anti-MSLN antibody with and without administration of 200 ug of anti-CD47 antibody 7, 10, and 13 days following adhesion induction. We saw a decrease in adhesion burden to our button site using anti-MSLN alone (FIG. 4D) in comparison to vehicle controls (FIG. 4C), and even greater reduction using anti-MSLN in association with anti-CD47 (FIG. 4E). Immunohistological analysis on buttons dissected from antibody treated mice showed collagen, fibronectin, and CD31 staining, but a lack of MSLN+ cells (FIG. 4F), suggesting removal of these cells and with them the adhesion tissue. These results indicate that targeted antibody therapy is a potential avenue for treatment post-adhesion formation.

Figure 6C:
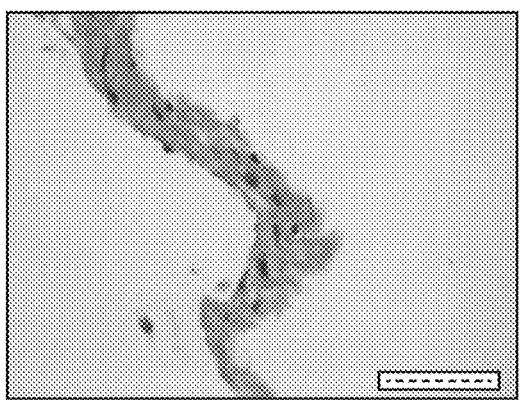
Figure 6C:
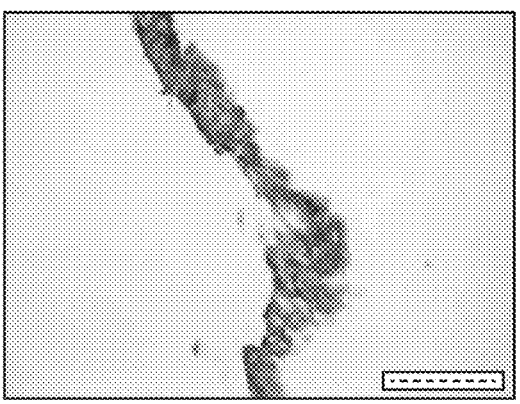
Figure 6C:
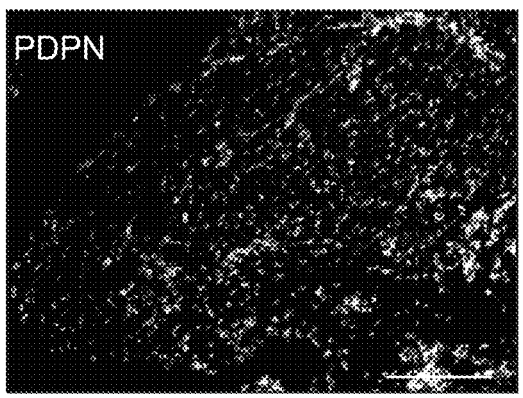
Figure 6C:
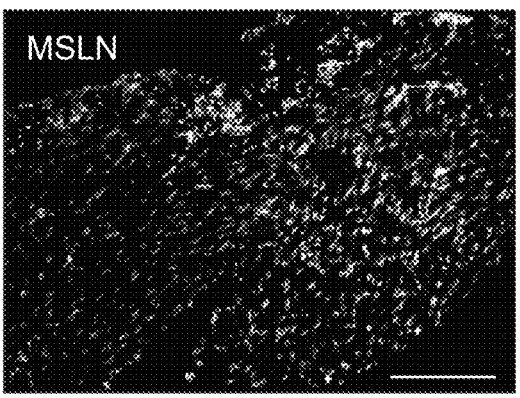
Figure 6C:
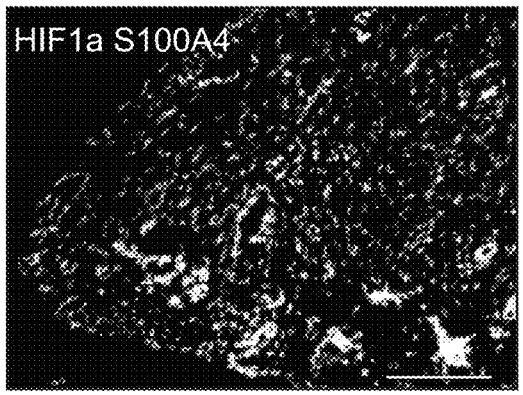
Figure 6C:
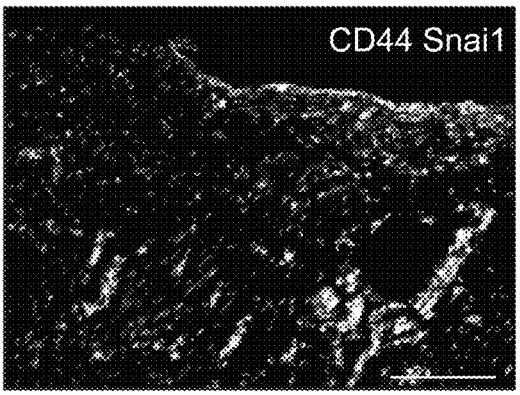
Figure 6C:
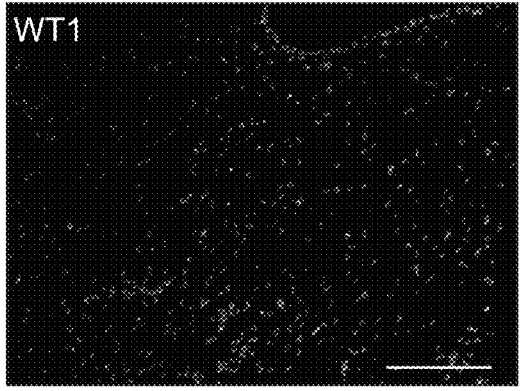
Figure 6C:
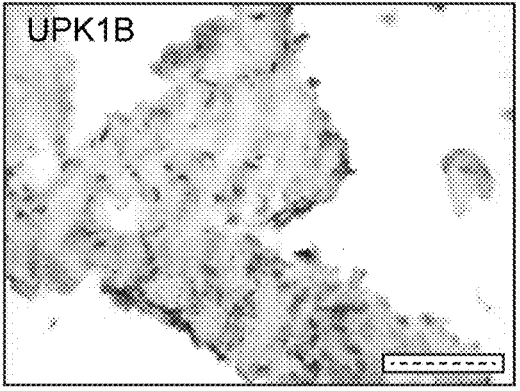

Our data illustrates a potential, hypoxia induced pathway in the mesothelial cell that is necessary for adhesion formation to occur. However, as many systems are governed differently in mouse and in human, we obtained human adhesion samples to determine whether our target genes were similarly expressed in human diseased tissue. We fixed, sectioned, and stained human adhesions with H&E and trichrome stains and observed a similar morphology; the adhesion was highly cellular and stained strongly for collagen deposition (FIG. 6A). Subsequent stains with PDPN, MSLN, HIF1A, S100A4, and WT1 (FIG. 6B) and in situ hybridization for UPK1B RNA demonstrate that many of our target genes are indeed expressed on human mesothelial tissue, suggesting that they may play a similar role in human adhesion formation.

Discussion

Through our work we believe we have achieved unprecedented cellular resolution of adhesion formation. Our current knowledge remains ambiguous as to the cellular origins for abdominal adhesions. Using specific stains and proliferation assays, we have discovered that surface mesothelium is the tissue-of-origin for abdominal adhesions and that the mechanistic basis of adhesion formation are rooted in programs of mesothelium cells, and potentially even further in mesothelium cell subsets.

Our sequencing studies have also offered unprecedented molecular resolution of the adhesion program. By focusing on the adhesion's tissue of origin, we have employed a panel of surface receptors combined with flow cytometry methods to isolate mesothelial cells in vivo. We have preserved its transcriptional programs and used RNA sequencing approaches to determine which programs in the surface mesothelium contribute to adhesion formation, including the time course of molecular events that lead naïve surface mesothelium to form adhesions. Chief among these programs is the hypoxia-induced pathway whose inhibition is sufficient enough to prevent adhesion formation. However, we should not ignore other unexplored programs, such as the early upregulation of angiogenesis, the steadily increased expression of various chemokines, and the early downregulation of extracellular matrix proteins and collagens. These data hint at a global phenomena underlying adhesion formation that involves other organ systems and tissues besides the mesothelium whose cooperation results in adhesion pathology.

The RNA sequencing data from purified mesothelium demonstrate a diverse signaling cascade that occurs following induction and begins to outline pathways within the mesothelium that contribute towards adhesion induction. We noticed that the mesothelial response is characterized by the re-expression of the embryonic mesothelial markers MSLN, uroplakin 1B (UPK1B), and Wilms Tumor 1 (WT1) This is not entirely surprising as embryonic phenotypes are often re-expressed during injury or malignancy. Injured mesothelium also upregulates expression of fibrocytic genes S100A4 and ACTA2, which, together with our in vivo staining and in vitro results, suggest that it is the mesothelium that becomes a fibroblast like cell. Finally, the expression of HIF1A reflects the hypoxic environment initiated by the adhesion induction protocol, which in turn mimics procedures done during surgical operations. What is striking however, is the significant effect that inhibition of HIF1A demonstrates on adhesion formation. Disruption of the HIF1A pathway by small molecule inhibitors echinomycin and or PX12 is sufficient to lead to a dramatic decrease in adhesion formation and frequency, suggesting that HIF1A plays an important role in the pathogenesis of adhesion formation.

Limited research has been done establishing the role of HIF1A in adhesion formation and even less in implicating the mesothelium as a key driver in this cascade. A few groups have shown the use of HIF1A inhibition in addressing adhesions, but these studies make use of RNA interference (RNAi) and or transgenic animal models. To our knowledge our study is the first to demonstrate the use of HIF1A inhibition using small molecule inhibitors, a treatment option much more suitable for clinical therapeutic use. Our data proposes the use of echinomycin, a peptide antibiotic, and or PX12, both of which are easily administrable in a clinical setting. However, as HIF1A is a general transcription factor, more work needs to be done to elucidate this pathway to devise a more targeted therapeutic approach. The in vivo model can provide a functional platform interrogate the molecular biology underlying the mesothelial contribution to adhesion pathogenesis.

We have also demonstrated an in vitro system as a substitute for our in vivo adhesion induction surgery. By co-culturing mesothelial explants from the renal capsule and intestines with macrophages in hypoxic conditions, we were able to create an adhesion-like phenotype, characterized by increased cellular density and fibrocytic change. Other hematopoietic cell types such as neutrophils and monocytes may be co-cultured with mesothelial cells. Stressors other that hypoxia such as mechanical perturbations or chemical or microorganismal challenges may induce similar responses. An in vitro system is useful to screen and identify molecular targets, and can provide a platform for drug discovery in regards to adhesion pathogenesis.

We have identified multiple adhesion specific molecules. Many of these are embryonic mesothelial genes that are re-expressed during injury and in few other tissues, making them prime targets for post formation treatments. With the identification of adhesion specific targets, we have demonstrated that the use of an antibody-based immunotherapy provides a therapeutic approach for the treatment of already formed adhesions.

EXAMPLE 2

A Neutrophil and Monocyte Axis Contributes Towards Adhesion Formation

Figure 9A:
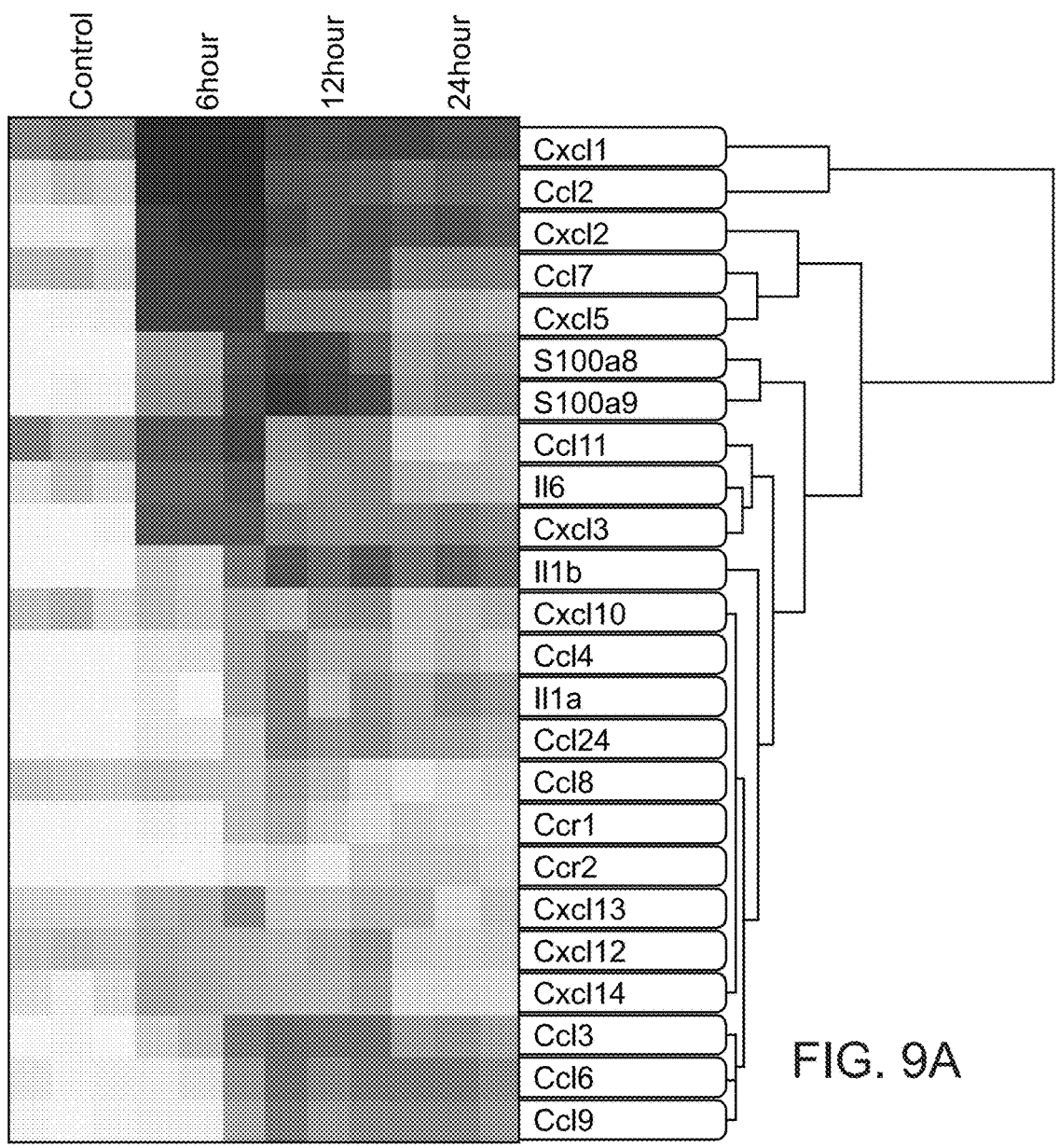
FIG. 9A-9D.
Figure 9B:
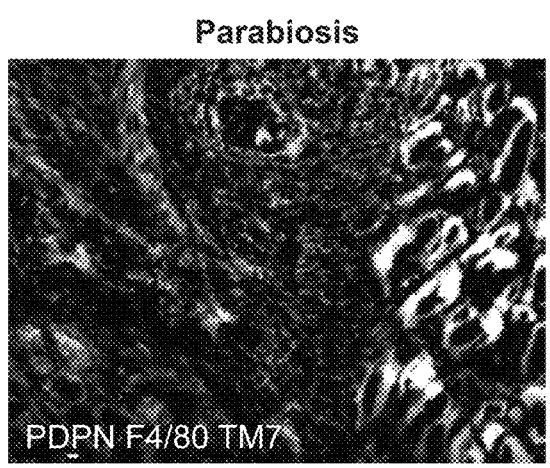
Figure 9C:
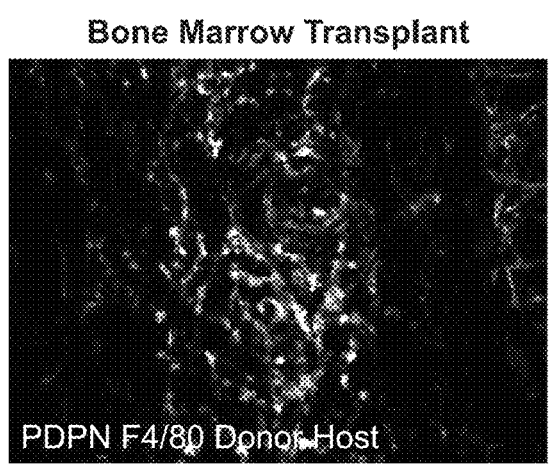
Figure 9D:
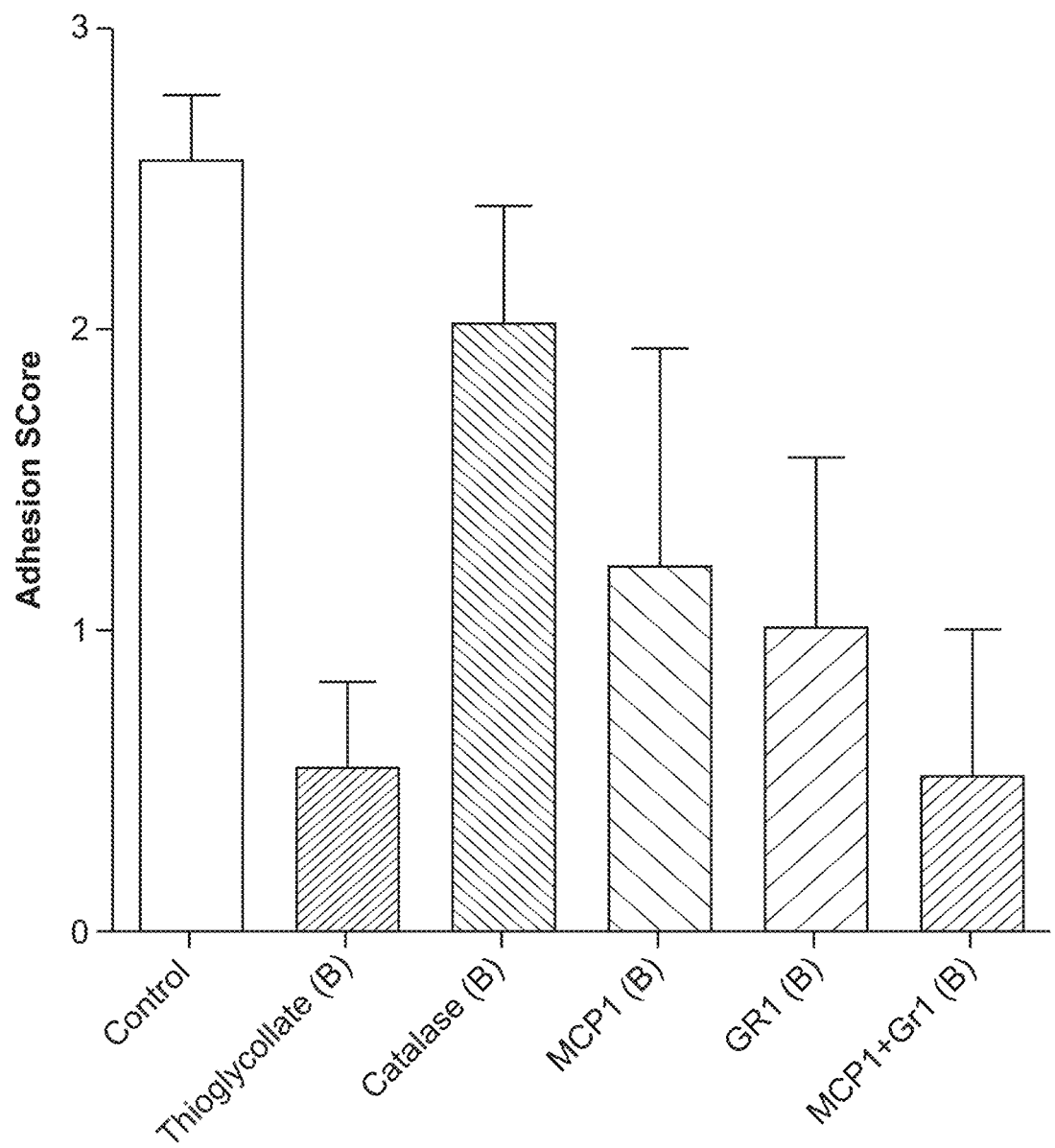

RNA sequencing results from injured mesothelial cells over a 24 hour time course were taken from previous experiments (see Example 1) and showed differential expression of multiple genesets and processes, including inflammatory chemokines and cytokines (FIG. 9A). Specific neutrophil and macrophage recruitment signals, CXCL1, CCL2, and CXCL2, are immediately upregulated after 6 hours and stay increased over the first 24 hours. Peritoneal washes from similar time points confirmed that increased numbers of neutrophils and macrophages enter the peritoneum. Although previous studies have demonstrated that neutrophils and macrophages respond to and are involved in adhesion pathogenesis, little work has been done demonstrating which subsets of these hematopoietic cells play key roles. Adhesion induction, as previously described in Example 1, in parabiosis experiments between a mouse constitutively expressing the red fluorescent protein mCherry ("TM7") and a wild type (non-colored mouse) showed red F4/80+ cells infiltrating the adhesion sites in a wild type mouse, suggesting that the macrophages that enter the adhesions are circulating monocytes, or bone marrow derived (FIG. 9B). Adhesion inductions in constitutive cyan fluorescent protein (CFP) mice ("Host") receiving bone marrow transplants from constitutive mCherry mice (TM7 "Donor") also show red F4/80+ cells in adhesion sites, again suggesting that macrophages entering the adhesions are circulating bone marrow derived monocytes (FIG. 9C). Mice treated with thioglycollate 24 hours prior to adhesion induction show diminished adhesions, indicating that sterile inflammation may have beneficial effects towards adhesion formation. Catalase treatment, which provides neutrophils a selective advantage over macrophages, 24 hours prior to adhesion induction, worsens adhesion formation in comparison to the thioglycollate treatment. Treatment with MCP-1, a known monocyte chemoattractant, and anti-GR-1 antibodies, resulting in depletion of circulating neutrophils, for three days following adhesion induction surgery both diminish adhesion formation. MCP1 in conjunction with anti-GR-1 has an additive effect in diminishing adhesion formation (FIG. 9D).

EXAMPLE 3

Figure 10:
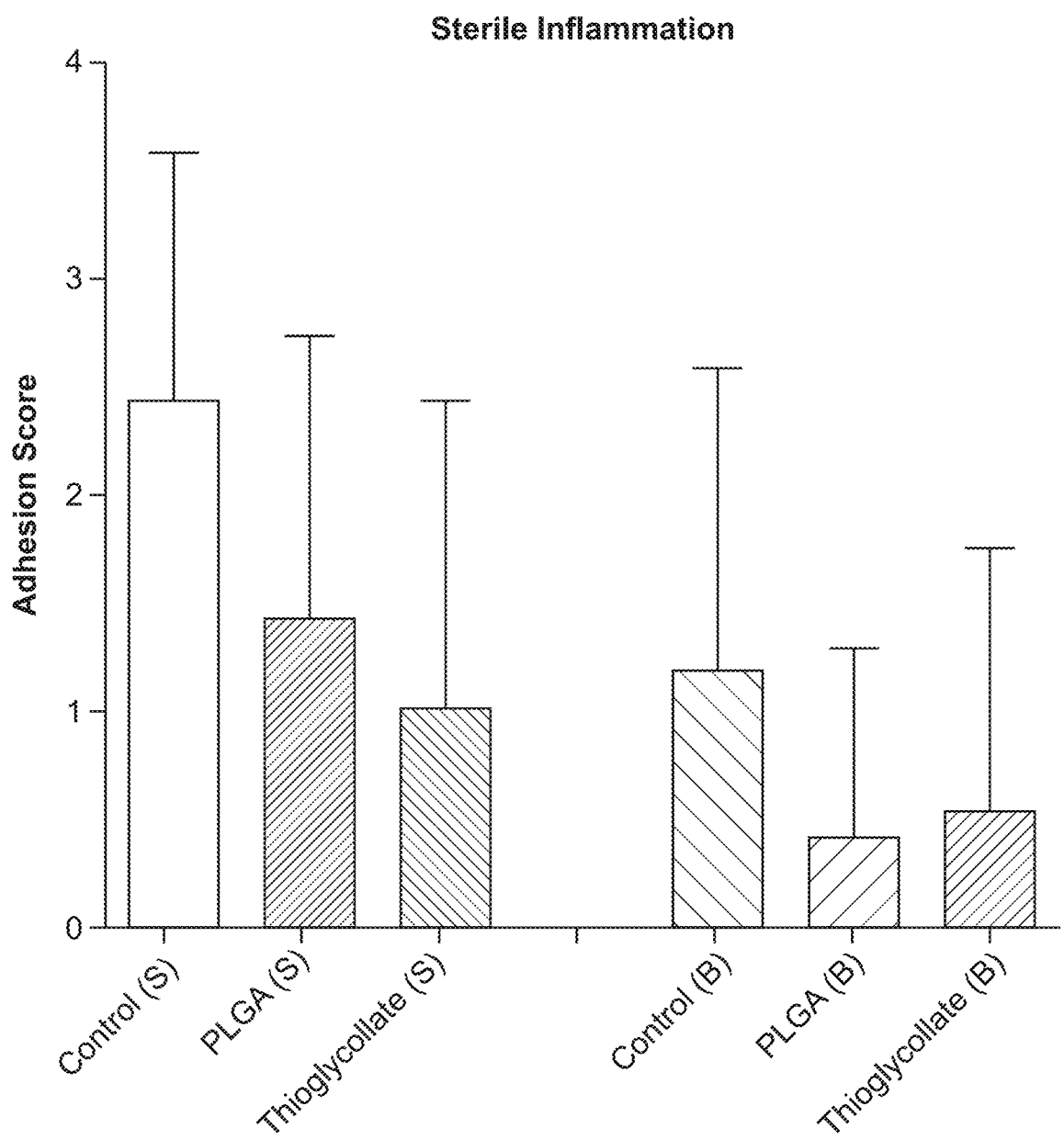
FIG. 10: Adhesion scores of mice pre-treated with either PLGA, thioglycollate, or PBS control 3 days prior to adhesion induction surgery. Mice were evaluated 7 days post injury and evaluated on an adhesion severity scale from 0-5 for adhesions forming on the suture site (S) or the button (B).

Mice were pre-treated with either PLGA, thioglycollate, or PBS control 3 days prior to adhesion induction surgery as described in Example 1. Mice were evaluated 7 days post injury and evaluated on an adhesion severity scale from 0-5 for adhesions forming on the suture site (S) or the button (B). FIG. 10 shows that mice pretreated with PLGA or thioglycollate have significantly reduced severity of adhesions at both the suture site and button. We conclude that pretreatment with PLGA alone, thioglycollate alone, or a combination of PLGA and thioglycollate prior to surgery will reduce the formation and/or severity of adhesions in a subject.

REFERENCES

1. Ward, B. C. & Panitch, A. Abdominal adhesions: current and novel therapies. J. Surg. Res. 165, 91-111 (2011).
2. Ghellai, A. Role of transforming growth factor beta-1 in peritonitis-induced adhesions,. J. Gastrointest. Surg. 4, 316-323 (2000).
3. Parker, M. C. et al. Colorectal surgery: the risk and burden of adhesion-related complications. Colorectal Dis. 6, 506-11 (2004).
4. Hershlag, A., Diamond, M. P. & DeCherney, A. H. Adhesiolysis. Clin. Obstet. Gynecol. 34, 395-402 (1991).
5. Ellis, H. et al. Adhesion-related hospital readmissions after abdominal and pelvic surgery: a retrospective cohort study. Lancet (London, England) 353, 1476-80 (1999).
6. Liakakos, T., Thomakos, N., Fine, P. M., Dervenis, C. & Young, R. L. Peritoneal adhesions: etiology, pathophysiology, and clinical significance. Recent advances in prevention and management. Dig. Surg. 18, 260-73 (2001).
7. Schnüriger, B. et al. Prevention of postoperative peritoneal adhesions: a review of the literature. Am. J. Surg. 201, 111-121 (2011).
8. Parker, M. C. et al. The SCAR-3 study: 5-year adhesion-related readmission risk following lower abdominal surgical procedures. Colorectal Dis. 7, 551-8 (2005).
9. Parker, M. C. et al. Postoperative adhesions: ten-year follow-up of 12, 584 patients undergoing lower abdominal surgery. Dis. Colon Rectum 44, 822-29; discussion 829-30 (2001).
10. Ray, N. F., Denton, W. G., Thamer, M., Henderson, S. C. & Perry, S. Abdominal adhesiolysis: inpatient care and expenditures in the United States in 1994. J. Am. Coll. Surg. 186, 1-9 (1998).
11. Chung, D. R. CD4+ T Cells Regulate Surgical and Postinfectious Adhesion Formation. J. Exp. Med. 195, 1471-1478 (2002).
12. Rinkevich, Y. et al. Identification and prospective isolation of a mesothelial precursor lineage giving rise to smooth muscle cells and fibroblasts for mammalian internal organs, and their vasculature. Nat. Cell Biol. 14, 1251-60 (2012).
13. Trochsler, M. & Maddern, G. J. Adhesion barriers for abdominal surgery: a sticky problem. Lancet (London, England) 383, 8-10 (2014).

14. Suzuki, T. et al. An injured tissue affects the opposite intact peritoneum during postoperative adhesion formation. Sci. Rep. 5, 7668 (2015).

Cassidy, M. R., Sherburne, A. C., Heydrick, S. J., & Stucchi, A. F. (2015). Combined intraoperative administration of a histone deacetylase inhibitor and a neurokinin-1 receptor antagonist synergistically reduces intra-abdominal adhesion formation in a rat model. Surgery, 157(3), 581-589. doi:10.1016/j.surg.2014.09.031

Chao, M. P., Alizadeh, A. A., Tang, C., Myklebust, J. H., Varghese, B., Gill, S., . . . Majeti, R. (2010). Anti-CD47 antibody synergizes with rituximab to promote phagocytosis and eradicate non-Hodgkin lymphoma. Cell, 142(5), 699-713. doi:10.1016/j.cell.2010.07.044

Chao, M. P., Weissman, 1. L., & Majeti, R. (2012). The CD47-SIRPα pathway in cancer immune evasion and potential therapeutic implications. Current Opinion in Immunology, 24(2), 225-32. doi:10.1016/j.coi.2012.01.010

Cheong, Y. C., Laird, S. M., Li, T. C., Shelton, J. B., Ledger, W. L., & Cooke, I. D. Peritoneal healing and adhesion formation/reformation. Human Reproduction Update, 7(6), 556-66. Retrieved from http://www.ncbi.nlm.nih.gov/pubmed/11727864

Chung, D. R. (2002). CD4+ T Cells Regulate Surgical and Postinfectious Adhesion Formation. Journal of Experimental Medicine, 195(11), 1471-1478. doi:10.1084/jem.20020028

Dat, N. T., Jin, X., Lee, J.-H., Lee, D., Hong, Y.-S., Lee, K., . . . Lee, J. J. (2007). Abietane diterpenes from Salvia miltiorrhiza inhibit the activation of hypoxia-inducible factor-1. Journal of Natural Products, 70(7), 1093-7. doi:10.1021/np060482d Dinarvand, P., Hassanian, S. M., Weiler, H., & Rezaie, A. R. (2015). Intraperitoneal administration of activated protein C prevents postsurgical adhesion band formation. Blood, 125(8), 1339-48. doi:10.1182/blood-2014-10-609339 diZerega, G. S., & Campeau, J. D. Peritoneal repair and post-surgical adhesion formation. Human Reproduction Update, 7(6), 547-55. Retrieved from http://www.ncbi.nlm.nih.gov/pubmed/11727863

Ellis, H., Harrison, W., & Hugh, T. B. (1965). The healing of peritoneum under normal and pathological conditions. British Journal of Surgery, 52(6), 471-476. doi:10.1002/bjs.1800520616

Hellebrekers, B. W. J., & Kooistra, T. (2011). Pathogenesis of postoperative adhesion formation. The British Journal of Surgery, 98(11), 1503-16. doi:10.1002/bjs.7657

Inagaki, N. F., Inagaki, F. F., Kokudo, N., & Miyajima, A. (2015). Use of mouse liver mesothelial cells to prevent postoperative adhesion and promote liver regeneration after hepatectomy. Journal of Hepatology, 62(5), 1141-7. doi:10.1016/j.jhep.2014.12.010

Jaiswal, S., Jamieson, C. H. M., Pang, W. W., Park, C. Y., Chao, M. P., Majeti, R., . . . Weissman, I. L. (2009). CD47 is upregulated on circulating hematopoietic stem cells and leukemia cells to avoid phagocytosis. Cell, 138(2), 271-85. doi:10.1016/j.cell.2009.05.046

Kim, Y. H., Coon, A., Baker, A. F., & Powis, G. (2011). Antitumor agent PX-12 inhibits HIF-1α protein levels through an Nrf2/PMF-1-mediated increase in spermidine/spermine acetyl transferase. Cancer Chemotherapy and Pharmacology, 68(2), 405-13. doi:10.1007/s00280-010-1500-0

Kong, D., Park, E. J., Stephen, A. G., Calvani, M., Cardellina, J. H., Monks, A., . . . Melillo, G. (2005). Echinomycin, a small-molecule inhibitor of hypoxia-inducible factor-1 DNA-binding activity. Cancer Research, 65(19), 9047-55. doi:10.1158/0008-5472.CAN-05-1235

Kosaka, H., Yoshimoto, T., Yoshimoto, T., Fujimoto, J., & Nakanishi, K. (2008). Interferon-gamma is a therapeutic target molecule for prevention of postoperative adhesion formation. Nature Medicine, 14(4), 437-41. doi:10.1038/nm1733

Liu, Y., Li, H., Shu, X. Z., Gray, S. D., & Prestwich, G. D. (2005). Crosslinked hyaluronan hydrogels containing mitomycin C reduce postoperative abdominal adhesions. Fertility and Sterility, 83 Suppl 1(4), 1275-83. doi:10.1016/j.fertnstert.2004.09.038

Lucas, P. A., Warejcka, D. J., Young, H. E., & Lee, B. Y. (1996). Formation of abdominal adhesions is inhibited by antibodies to transforming growth factor-beta1. The Journal of Surgical Research, 65(2), 135-8. doi:10.1006/jsre.1996.0355

Michailova, K. N., & Usunoff, K. G. (2006). Serosal membranes (pleura, pericardium, peritoneum). Normal structure, development and experimental pathology. Advances in Anatomy, Embryology, and Cell Biology, 183, i-vii, 1-144, back cover. Retrieved from http://www.ncbi.nlm.nih.gov/pubmed/16570866

Moreno-Manzano, V., Rodriguez-Jiménez, F. J., Aceña-Bonilla, J. L., Fustero-Lardies, S., Erceg, S., Dopazo, J., . . . Sánchez-Puelles, J. M. (2010). FM19G11, a new hypoxia-inducible factor (HIF) modulator, affects stem cell differentiation status. The Journal of Biological Chemistry, 285(2), 1333-42. doi:10.1074/jbc.M109.008326

Raftery, A. T. (1973). Regeneration of parietal and visceral peritoneum: an electron microscopical study. Journal of Anatomy, 115(Pt 3), 375-92. Retrieved from http://www.pubmedcentral.nih.gov/articlerender.fcgi?artid=1271-491&tool=pmcentrez&rendertyp e=abstract Ray, N. (1998). Abdominal Adhesiolysis: Inpatient Care and Expenditures in the United States in 1994. Journal of the American College of Surgeons, 186(1), 1-9. doi:10.1016/51072-7515(97)00127-0

Richardson, E. H. (1911). IV. Studies on Peritoneal Adhesions: With a Contribution to the Treatment of Denuded Bowel Surfaces. Annals of Surgery, 54(6), 758-97. Retrieved from http://www.pubmedcentral.nih.gov/articlerender.fcgi?artid=1406358&tool=pmcentrez&rendertyp e=abstract Rinkevich, Y., Mori, T., Sahoo, D., Xu, P.-X., Bermingham, J. R., & Weissman, I. L. (2012). Identification and prospective isolation of a mesothelial precursor lineage giving rise to smooth muscle cells and fibroblasts for mammalian internal organs, and their vasculature. Nature Cell Biology, 14(12), 1251-60. doi:10.1038/ncb2610

Rinkevich, Y., Walmsley, G. G., Hu, M. S., Maan, Z. N., Newman, A. M., Drukker, M., . . . Longaker, M. T. (2015). Skin fibrosis. Identification and isolation of a dermal lineage with intrinsic fibrogenic potential. Science (New York, N.Y.), 348(6232), aaa2151. doi:10.1126/science.aaa2151

Schade, D. S., & Williamson, J. R. (1968). The pathogenesis of peritoneal adhesions: an ultrastructural study. Annals of Surgery, 167(4), 500-10. Retrieved from http://www.pubmedcentral.nih.gov/articlerender.fcgi?artid=13872-40&tool=pmcentrez&rendertyp e=abstract Suzuki, A. (2015). Evidence of cell-fate conversion from hepatocytes to cholangiocytes in the injured liver: in-vivo genetic lineage-tracing approaches. Current Opinion in Gastroenterology. doi:10.1097/MOG.0000000000000172

Suzuki, T., Kono, T., Bochimoto, H., Hira, Y., Watanabe, T., & Furukawa, H. (2015). An injured tissue affects the opposite intact peritoneum during postoperative adhesion formation. Scientific Reports, 5, 7668. doi:10.1038/srep07668

Tseng, D., Volkmer, J.-P., Willingham, S. B., Contreras-Trujillo, H., Fathman, J. W., Fernhoff, N. B., . . . Weissman, I. L. (2013). Anti-CD47 antibody-mediated phagocytosis of cancer by macrophages primes an effective antitumor T-cell response. Proceedings of the National Academy of Sciences of the United States of America, 110(27), 11103-8. doi:10.1073/pnas.1305569110

Ueno, H., & Weissman, I. L. (2006). Clonal analysis of mouse development reveals a polyclonal origin for yolk sac blood islands. Developmental Cell, 11(4), 519-33. doi:10.1016/j.devcel.2006.08.001

Wang, C., Li, X., Meng, X., Zhou, J., Qin, F., & Hou, L. (2014). Prevention of experimental postoperative peritoneal adhesions through the intraperitoneal administration of tanshinone IIA. Planta Medica, 80(12), 969-73. doi:10.1055/s-0034-1382877

Wei, G., Chen, X., Wang, G., Jia, P., Xu, Q., Ping, G., . . . Li, X. (2015). Inhibition of cyclooxygenase-2 prevents intra-abdominal adhesions by decreasing activity of peritoneal fibroblasts. Drug Design, Development and Therapy, 9, 3083-98. doi:10.2147/DDDT.S80221

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject to reduce adhesion formation, the method comprising administering to a subject in need thereof:
   a combination of an antibody that binds to mesothelin (MSLN) and an antibody that binds to CD47 and disrupts the binding of CD47 with SIRPα, at a dose that achieves a depletion of injured mesothelial cells.

2. The method of claim 1, wherein the combination of an antibody that binds to mesothelin (MSLN) and an antibody that binds to CD47 is administered prior to a surgical procedure performed on the subject.

3. A method of treating a subject to reduce already-formed adhesions, the method comprising administering to a subject in need thereof:
   a combination of an antibody that binds to mesothelin (MSLN) and an antibody that binds to CD47 and disrupts the binding of CD47 with SIRPα, at a dose that achieves a depletion of injured mesothelial cells.

4. The method of claim 3, wherein the adhesion is an abdominal adhesion.

5. The method of claim 3, wherein the adhesion is a surgical adhesion.

6. The method of claim 5, wherein the combination of an antibody that binds to mesothelin (MSLN) and an antibody that binds to CD47 is administered after a surgical procedure performed on the subject.

* * * * *

UNITED STATES PATENT AND TRADEMARK OFFICE
CERTIFICATE OF CORRECTION

Page 1 of 1

PATENT NO. : 10,934,355 B2
APPLICATION NO. : 16/079927
DATED : March 2, 2021
INVENTOR(S) : Jonathan Tsai et al.

It is certified that error appears in the above-identified patent and that said Letters Patent is hereby corrected as shown below:

In the Specification

In Column 1, Lines 17-20, please replace the STATEMENT OF GOVERNMENT SUPPORT section with the following:
--This invention was made with Government support under contracts DK108561, GM007365, and HL099999 awarded by the National Institutes of Health. The Government has certain rights in the invention.--

Signed and Sealed this
Tenth Day of February, 2026

John A. Squires
*Director of the United States Patent and Trademark Office*